(12) United States Patent
Corti

(10) Patent No.: US 7,622,105 B2
(45) Date of Patent: *Nov. 24, 2009

(54) MODIFIED CYTOKINES FOR USE IN CANCER THERAPY

(75) Inventor: Angelo Corti, Milan (IT)

(73) Assignee: Fondazione Centro San Raffaele Del Monte Tabor, Milan (IT)

( * ) Notice: Subject to any disclaimer, the term of this patent is extended or adjusted under 35 U.S.C. 154(b) by 346 days.

This patent is subject to a terminal disclaimer.

(21) Appl. No.: 11/338,842

(22) Filed: Jan. 25, 2006

(65) Prior Publication Data

US 2006/0115451 A1 Jun. 1, 2006

Related U.S. Application Data

(60) Division of application No. 10/426,019, filed on Apr. 30, 2003, now Pat. No. 7,109,303, which is a continuation-in-part of application No. 10/287,811, filed on Nov. 5, 2002, now Pat. No. 7,309,694, which is a continuation-in-part of application No. 10/218,906, filed on Aug. 15, 2002, now Pat. No. 7,150,869, which is a continuation-in-part of application No. PCT/EP01/01543, filed on Feb. 13, 2001.

(30) Foreign Application Priority Data

Feb. 15, 2000 (IT) .............................. MI00A0249

(51) Int. Cl.
*A61K 38/00* (2006.01)
*A61K 38/19* (2006.01)
*A61K 38/21* (2006.01)

(52) U.S. Cl. ................... 424/85.1; 424/85.5; 424/185.1; 514/2; 514/12; 514/9; 514/16; 514/17

(58) Field of Classification Search ........................ None
See application file for complete search history.

(56) References Cited

U.S. PATENT DOCUMENTS

| | | | |
|---|---|---|---|
| 4,650,674 A | 3/1987 | Aggarwal et al. | |
| 4,791,101 A | 12/1988 | Adolf | |
| 5,258,517 A | 11/1993 | Zepp et al. | |
| 5,539,063 A | 7/1996 | Hakimi et al. | |
| 5,811,388 A | 9/1998 | Friend et al. | |
| 5,888,814 A | 3/1999 | Kriegler et al. | |
| 6,180,084 B1 | 1/2001 | Ruoslahti et al. | |
| 6,576,239 B1 | 6/2003 | Ruoslahti et al. | |
| 6,759,509 B1 | 7/2004 | King et al. | |

FOREIGN PATENT DOCUMENTS

| | | |
|---|---|---|
| EP | 0 251 494 A2 | 1/1988 |
| EP | 0 496 074 A1 | 7/1992 |
| WO | WO 95/15979 A1 | 6/1995 |
| WO | WO 98/10795 A2 | 3/1998 |
| WO | WO 99/13329 A1 | 3/1999 |
| WO | WO 01/61017 A2 | 8/2001 |

OTHER PUBLICATIONS

Lohn et al. (Leuk. Lymphoma, 2002, 43(2):407-413).*
Tabata et al., "Targeting of Tumor Necrosis Factor to Tumor by Use of Dextran and Metal Coordination," *Journal of Controlled Release* 59, 1999, pp. 187-196.
Miyata et al., "Overcoming the Metastasis-Enhancing Potential of Human Tumor Necrosis Factor α by Introducing the Cell-Adhesive Arg-Gly-Asp Sequence," 1995, pp. 161-169.
Hottiger, Mo, et al., "Liposome-mediated gene transfer into human basal cell carcinoma", *Gene Therapy*, 1999, 6:1929-1935.
Flavio Curnis, et al., "*Enhancement Of Tumor Necrosis Factor α Antitumor Immunotherapeutic Properties By Targeted Delivery To Aminopeptidase N (CD13)*", Nature Biotechnology vol. 18, Nov. 2000, pp. 1185-1190.
Helson, et al., Effect of Tumor Necrosis Factor on Cultured Human Melanoma Cells, *Nature* 1975, 258, pp. 731-732.
Schraffordt et al., Hyperthermic Isolated Limb Perfusion with Tumour Necrosis Factor and Melphalan as Treatment of Locally Advanced or Recurrent Soft Tissue Sarcomas of the Extremities, Radiotherapy & Oncology 1998, 48: pp. 1-4.
Pennica, et al., "Cloning and expression in *Escherichia coli* of the cDNA for murine tumor necrosis factor," *Proc. Natl. Acad. Sci. USA*, 82:6060-6064 (1985), USA.
Ostade, et al., "Human TNF mutants with selective activity on the p55 receptor," *Nature*, 361:266-269 (1993), Belgium.
Koops, et al., "Hyperthermic isolated limb perfusion with tumour necrosis factor and melphalan as treatment of locally advanced or recurrent soft tissue sarcomas of the extremities," *Radiotherapy and Oncology*, 48:1-4 (1998), Elsevier Science Ireland Ltd., UK.
Arap, et al., "Cancer Treatment by Targeted Drug Delivery to Tumor Vasculature in a Mouse Model," *Science*, 279:377-381 (1998), USA.
Liénard, et al., "In Transit Metastases of Malignant Melanoma Treated by High Dose rTNFα in Combination with Interferon-γ and Melphalan in Isolation Perfusion," *World J. Surg.*, 16:234-240 (1992), Societe Internationale de Chirurgie, Belgium.
Corti, et al., "Upregulation of p75 Tumor Necrosis Factor Alpha Receptor in *Mycobacterium avium*-Infected Mice: Evidence for a Functional Role," *Infection and Immunity*, 67(11):5762-5767 (1999), American Society for Microbiology.
Loetscher, et al., "Human Tumor Necrosis Factor α (TNFα) Mutants with Exclusive Specificity for the 55-kDa or 75-kDa TNF Receptors," *The Journal of Biological Chemistry*, 268(35):26350-26357 (1993), The American Society for Biochemistry and Molecular Biology, Inc., USA.
Colombo, et al., "Immunoscintigraphy with anti-chromogranin A antibodies in patients with endocrine/neuroendocrine tumors," *J. Endocrinol. Invest.*, 16:841-843 (1993), Germany.
Ljunggren, et al., "Host Resistance Directed Selectively Against H-2-Deficient Lymphoma Variants," *J. Exp. Med.*, 162:1745-1759 (1985), The Rockefeller University Press, USA.

(Continued)

Primary Examiner—Daniel C Gamett
(74) *Attorney, Agent, or Firm*—Foley & Lardner LLP

(57) ABSTRACT

Cytokine derivatives capable of homing the tumoral vessels and the antigen presenting cells and the use thereof as antitumoral agents.

11 Claims, 15 Drawing Sheets

OTHER PUBLICATIONS

Corti, et al., "Tumor necrosis factor (TNF) α quantification by Elisa and bioassay: effects of TNFα-soluble TNF receptor (p55) complex dissociation during assay incubations," *Journal of Immunological Methods*, 177:191-198 (1994), Elsevier Science B.V., UK.

Palladino, et al., "Characterization of the Antitumor Activities of Human Tumor Necrosis Factor-α and the Comparison with Other Cytokines: Induction of Tumor-Specific Immunity," *The Journal of Immunology*, 138(11):4023-4032 (1987), The American Association of Immunologists, USA.

Debs, et al., "Immunomodulatory and Toxic Effects of Free and Liposome-encapsulated Tumor Necrosis Factor α in Rats," *Cancer Research*, 50:375-380 (1990), USA.

Moro, et al., "Tumor Cell Targeting with Antibody-Avidin Complexes and Biotinylated Tumor Necrosis Factor α," *Cancer Research*, 57:1922-1928 (1997), Italy.

Robert, et al., "Cytokine Targeting in Tumors Using a Bispecific Antibody Directed against Carcinoembryonic Antigen and Tumor Necrosis Factor α," *Cancer Research*, 56:4758-4765 (1996).

Debs, et al., "Liposome-Associated Tumor Necrosis Factor Retains Bioactivity in the Presence of Neutralizing Anti-Tumor Necrosis Factor Antibodies," *The Journal of Immunology*, 143(4), 1192-1197 (1989), The American Association of Immunologists, USA.

Hoogenboom, et al., "Construction and Expression of Antibody-Tumor Necrosis Factor Fusion Proteins," *Molecular Immunology*, 28(9):1027-1037 (1991), Pergamon Press, UK.

Yang, et al., "A Genetically Engineered Single-Chain FV/TNF Molecule Possesses the Anti-Tumor Immunoreactivity of FV as well as the Cytotoxic Activity of Tumor Necrosis Factor," *Mol. Immunol.*, 1995, 32:873-881, Elsevier Science Ltd., UK.

Eggermont, et al., "Isolated Limb Perfusion with Tumor Necrosis Factor and Melphalan for Limb Salvage in 186 Patients with Locally Advanced Soft Tissue Extremity Sarcomas," *Annals of Surgery*, 224(6):756-765 (1996), Lippincott-Raven Publishers.

Rathjen, et al., "Selective enhancement of the tumour necrotic activity of TNF, with monoclonal antibody," *Br. J. Cancer*, 65:857-864 (1992), Macmillan Press Ltd., USA.

Modorati, et al., Immunoscintigraphy with three step monoclonal pretargeting technique in diagnosis of uveal melanoma: preliminary results, *British Journal of Ophthalmol.*, 78:19-23 (1994), UK.

Hill, et al., Low-does tumour necrosis factor α and melphalan in hyperthermic isolated limb perfusion, *British J. Surg.*, 80:995-997 (1993), Butterworth-Heinemann Ltd, UK.

Paganelli, et al., "Three-Step Monoclonal Antibody Tumor Targeting in Carcinoembryonic Antigen-Positive Patients," *Cancer Research*, 51:5960-5966 (1991).

Paganelli, et al., "Clinical Application of the Avidin-Biotin System for Tumor Targeting," *Can. Therapy with Radiolabelled Antibodies*, 239-254 (1995), CRC Press, Inc., UK.

Gasparri, et al., "Tumor Pretargeting with Avidin Improves the Therapeutic Index of Biotinylated Tumor Necrosis Factor α in Mouse Models," *Cancer Research*, 59:2917-2923 (1999).

Mizuguchi, et al., "Tumor Necrosis Factor α-mediated Tumor Regression by the in vivo Transfer of Genes into the Artery That Leads to Tumors," *Cancer Research*, 58:5725-5730 (1998).

Corti, et al., "Tumor Targeting with Biotinylated Tumor Necrosis Factor α: Structure-Activity Relationships and Mechanism of Action on Avidin Pretargeted Tumor Cells," *Cancer Research*, 58:3866-3872 (1998).

Fiers, "Chapter 12 Biologic Therapy with TNF: Preclinical Studies," *Biologic Therapy of Cancer: Principles and Practice*, 1995, pp. 295-327, JB Lippincott Company, Phila., PA.

Fraker, et al., "Chapter 13 Biologic Therapy with TNF: Systemic Administration and Isolation-Perfusion," *Biologic Therapy of Cancer: Principles and Practice*, 1995, pp. 329-345, JB Lippincott Company, Phila., PA.

Pasqualini, et al., "Aminopeptidase N Is a Receptor for Tumor-homing Peptides and a Target for Inhibiting Angiogenesis," *Cancer Research*, 60:722-727, (2000).

Chen, et al., "Enhanced Anti-tumor Effect of an IFN-γ-EGF Fusion Protein," *Biomedical and Environmental Sciences*, 10:387-395 (1997), CAPM.

Curnis, et al., "Enhancement of tumor necrosis factor α antitumor immunotherapeutic properties by targeted delivery to aminopeptidase N (CD13)," *Nature Biotechnology*, 15:1185-1190 (2000), USA.

Pennica, et al., "Human tumour necrosis factor: precursor structure, expression and homology to lymphotoxin," *Nature*, 312:20-27 (1984), USA.

Celik, et al., "Demonstration of Immunogenicity with the Poorly Immunogenic B16 Melanoma," *Cancer Research*, 43:3507-3510 (1983), USA.

Carswell, et al., "An endotoxin-induced serum factor that causes necrosis of tumors," *Proc. Nat. Acad. Sci. USA*, vol. 72(9):3666-3670 (1975), USA.

Waldmann, et al., "Low dose unresponsiveness with a thymus independent antigen," *Nature*, 258:730-733 (1975).

Tracey, et al., "Tumor Necrosis Factor, Other Cytokines and Disease," *Annu. Rev. Cell Biol.* 9:317-343, (1993), Annual Reviews Inc., USA.

Curnis et al., "Targeted Delivery of Tumor Necrosis Factor Alpha (TNF) to Tumor Associated Vessels", International Journal of Molecular Medicine, Spandidos, Athens, GA, vol. 6, No. Suppl. 1, Oct. 19, 2000, p. S72, XP001030678, ISSN: 1107-3756.

Yilmaz et al., "Pulse treatment of human vascular endothelial cells with high doses of tumor necrosis factor and interferon-gamma results in simultaneous synergistic and reversible effects on proliferation and morphology", International Journal of Cancer. Journal International Du Cancer. United States, vol. 77, No. 4, Aug. 12, 1998, pp. 592-599, XP002279975, ISSN: 0020-7136.

Suk et al., "Interferon gamma (IFNgamma) and tumor necrosis factor alpha synergism in ME-180 cervical cancer cell apoptosis and necrosis. IFNgamma inhibits cytoprotective NF-kappa B through STAT1/IRF-1 pathways", The Journal of Biological Chemistry, United States, vol. 276, No. 16, Apr. 20, 2001, pp. 13153-13159, XP002279974, ISSN: 0021-9258.

Luck et al., *Molecular Endocrinology*, 1991, vol. 5(12), pp. 1880-1886.

Hattori et al., *J. Agric. Food Chem.*, 2000, vol. 48(9), pp. 3789-3794.

Kost et al., *Gynecol. Oncol.*, 1999, vol. 72(3), pp. 392-401.

Stein et al., *Cytotechnology*, 1998, vol. 27, pp. 271-282.

Pietersz et al., "In Vitro and In Vivo Evaluation of Human Tumor Necrosis Factor-α (hTNF α) Chemically Conjugated to Monoclonal Antibody," *J. Drug Target*, 5(2):109-120, 1998.

* cited by examiner

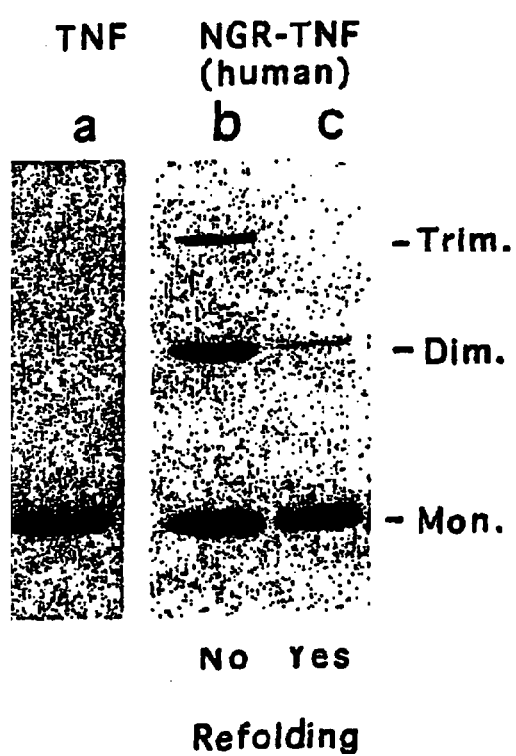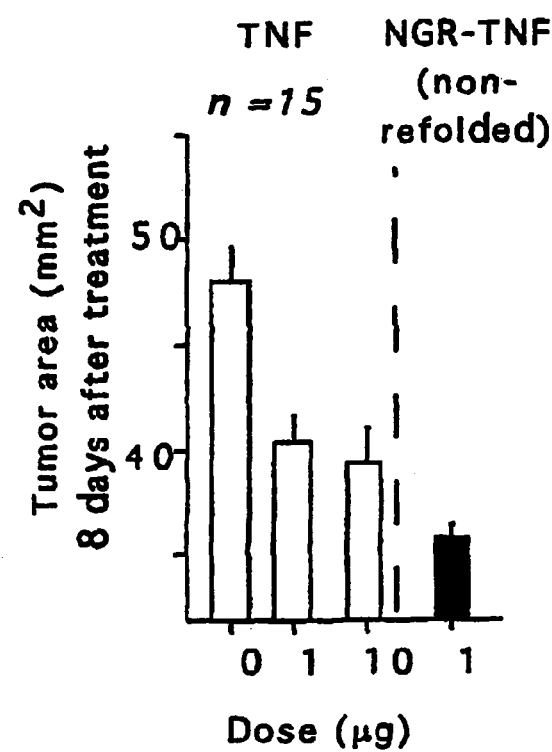
Fig. 4a
Fig. 4b

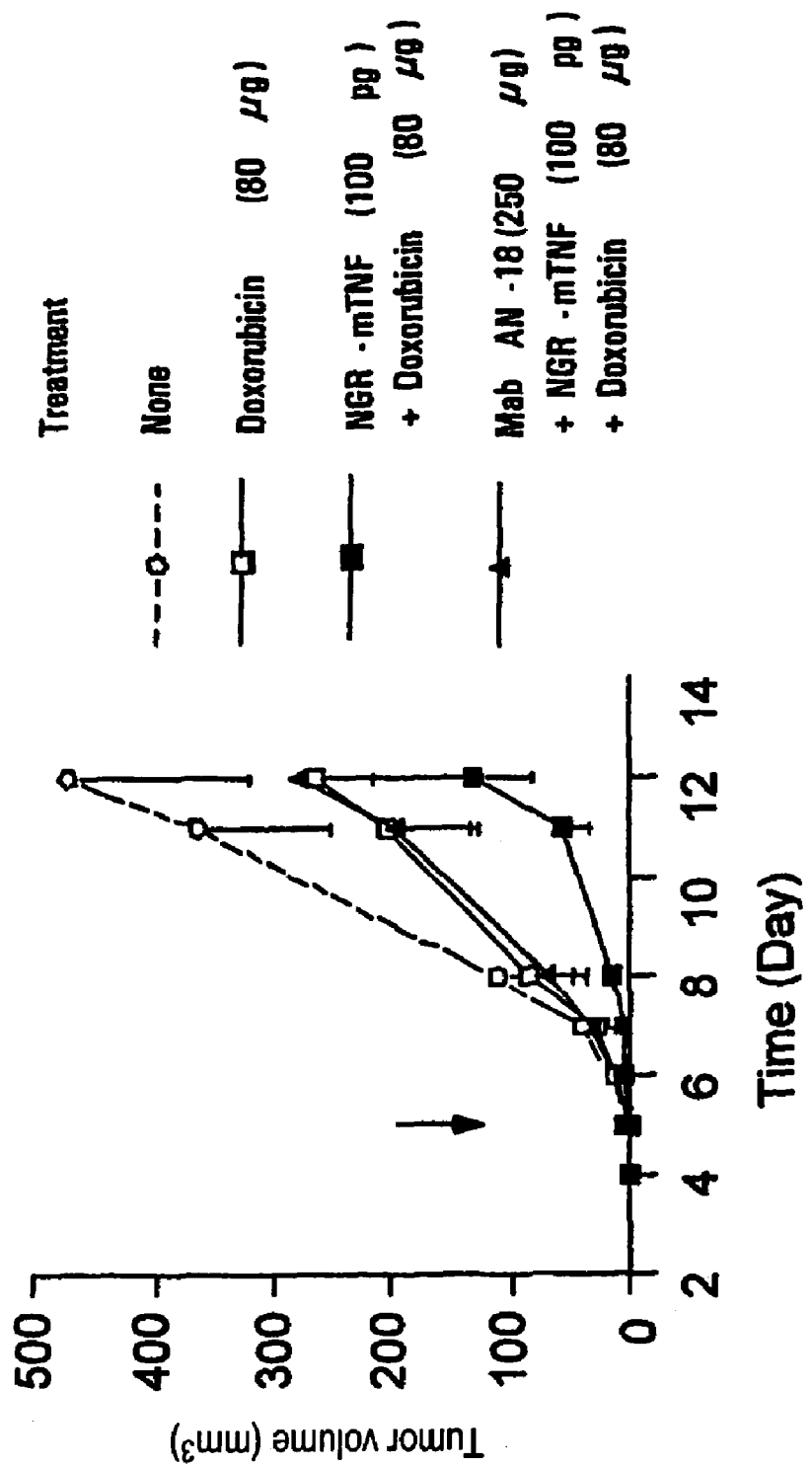

SEQUENCE LISTING

```
<160> NUMBER OF SEQ ID NOS: 19

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      NGR- peptide ligand

<400> SEQUENCE: 1

Cys Asn Gly Arg Cys Val Ser Gly Cys Ala Gly Arg Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      NGR- peptide ligand

<400> SEQUENCE: 2

Asn Gly Arg Ala His Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      NGR- peptide ligand

<400> SEQUENCE: 3

Gly Asn Gly Arg Gly
1               5

<210> SEQ ID NO 4
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      NGR- peptide ligand
<220> FEATURE:
<223> OTHER INFORMATION: Cyclic peptide

<400> SEQUENCE: 4

Cys Val Leu Asn Gly Arg Met Glu Cys
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      NGR- peptide ligand
<220> FEATURE:
<223> OTHER INFORMATION: Linear peptide

<400> SEQUENCE: 5

Cys Asn Gly Arg Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      NGR- peptide ligand
<220> FEATURE:
<223> OTHER INFORMATION: Cyclic peptide

<400> SEQUENCE: 6

Cys Asn Gly Arg Cys
1               5

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7
ctggatcctc acagagcaat gactccaaag                                      30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
tgcctcacat atgctcagat catcttctc                                       29

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      PCR primer
```

<400> SEQUENCE: 9
gcagatcata tgtgcaacgg ccgttgcggc ctcagatcat cttctc        46

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
atatcatatg tgcaacggcc gttgcggcgt cagatcatcd ttctcg        46

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 11
tcaggatcct cacagggcaa tgatcccaaa gtagac        36

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 12
atatctacat atgcacggca cagtcattga aagcc        35

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
tcggatcctc agcaacggcc gttgcagccg gagcgactcc ttttccgctt cctgaggc        58

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 14
agaattcatg aacgctacac actgcatctt ggc        33

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15

```
tatattaagc tttcagcagc gactcctttt ccgc                                34
```

```
<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      NGR-TNF peptide fragment

<400> SEQUENCE: 16

Cys Asn Gly Arg Cys Gly Leu Arg Ser Ser Ser Gln
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      NGR-TNF peptide fragment

<400> SEQUENCE: 17

Met Leu Arg Ser Ser Ser Gln
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      NGR TNF motif

<400> SEQUENCE: 18

Cys Asn Gly Arg Cys Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Ala Arg Ala Cys
  1             5
```

MODIFIED CYTOKINES FOR USE IN CANCER THERAPY

FIELD OF THE INVENTION

The present invention refers to modified cytokines for use in the treatment of cancer. More particularly, the invention refers to cytokines derivatives capable of "homing" tumor vessels and antigen presenting cells. The present invention also relates to synergistic combinations which include a modified cytokine.

BACKGROUND OF THE INVENTION

The antitumoral activity of some cytokines is well known and described. Some cytokines have already been used therapeutically also in humans (29). For example, such cytokines as interleukine-2 (IL-2) and interferon α(IFNα) have shown positive antitumoral activity in patients with different types of tumors, such as kidney metastatic carcinoma, hairy cell leukemia, Kaposi sarcoma, melanoma, multiple mieloma, and the like. Other cytokines like IFNβ, the Tumor Necrosis Factor (TNF) α, TNFβ, IL-1, 4, 6, 12, 15 and the Colony Stimulating Factors (CFSs) have shown a certain antitumoral activity on some types of tumors and therefore are the object of further studies.

In general, the therapeutic use of cytokines is strongly limited by their systemic toxicity. TNF, for example, was originally discovered for its capacity of inducing the hemorrhagic necrosis of some tumors (1), and for its in vitro cytotoxic effect on different tumoral lines (2), but it subsequently proved to have strong pro-inflammatory activity, which can, in case of overproduction conditions, dangerously affect the human body (3).

As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

Some novel approaches are directed to:
a) the development of fusion proteins which can deliver TNF into the tumor and increase the local concentration. For example, the fusion proteins consisting of TNF and tumor specific-antibodies have been produced (4);
b) the development of TNF mutants which maintain the antitumoral activity and have a reduced systemic toxicity. Accordingly, mutants able of selectively recognizing only one receptor (p55 or p75) have been already prepared (5);
c) the use of anti-TNF antibodies able to reduce some toxic effects of TNF without compromising its antitumoral activity. Such antibodies have been already described in literature (30);
d) the use of TNF derivatives with a higher half-life (for example TNF conjugated with polyethylene glycol).

The preparation of TNF derivatives capable of selectively targeting the tumoral sites has been recently reported. For example, a fusion protein has been described, obtained by fusing the gene of the heavy chain of an anti-transferrin receptor mAb and the TNF gene (4), or a fusion protein of TNF with the "hinge" region of a monoclonal antibody against the tumor-associated TAG72 antigen (6), or a Fv-TNF fusion protein (6).

EP 251 494 discloses a system for administering a diagnostic or therapeutic agent, which comprises: an antibody conjugated with avidin or streptavidin, an agent capable of complexing the conjugated antibody and a compound consisting of the diagnostic or therapeutic agent conjugated with biotin, which are administered sequentially and adequately delayed, so as to allow the localization of the therapeutic or diagnostic agent through the biotin-streptavidin interaction on the target cell recognized by the antibody. The described therapeutic or diagnostic agents comprise metal chelates, in particular chelates of radionuclides and low molecular weight antitumoral agents such as cis-platinum, doxorubicin, etc.

EP 496 074 discloses a method which provides the sequential administration of a biotinylated antibody, avidin or streptavidin and a biotinylated diagnostic or therapeutic agent. Although cytotoxic agents like ricin are generically mentioned, the application relative to radiolabelled compounds is mostly disclosed.

WO 95/15979 discloses a method for localizing highly toxic agents on cellular targets, based on the administration of a first conjugate comprising the specific target molecule conjugated with a ligand or an anti-ligand followed by the administration of a second conjugate consisting of the toxic agent bound to an anti-ligand or to the ligand.

WO98/10795 discloses tumor homing molecules including peptides containing the amino acid sequence NGR. No use of the peptide to target a cytokine to a tumor is described.

WO 99/13329 discloses a method for targeting a molecule to tumoral angiogenic vessels, based on the conjugation of said molecule with ligands of NGR receptors. A number of molecules have been suggested as possible candidates, but doxorubicin only is specifically described. No use of ligands of NGR receptors as cytokines vehicles to induce immuno responses is disclosed.

SUMMARY OF THE INVENTION

It has now surprisingly been found that the therapeutic index of certain cytokines can be remarkably improved and their immunotherapeutic properties can be enhanced by coupling with a ligand of aminopeptidase-N receptor (CD13). CD13 is a trans-membrane glycoprotein of 150 kDa highly conserved in various species. It is expressed on normal cells as well as in myeloid tumor lines, in the angiogenic endothelium and is some epithelia. CD13 receptor is usually identified as "NGR" receptor, in that its peptide ligands share the amino acidic "NGR" motif. We have also surprisingly found that TNF coupled with a ligand of CD13 receptor and IFNγ act synergistically so that effective anti-tumor activity may be seen upon co-administration at dosages which are below the effective doses individually. In addition, we have found that the anti-tumor activity of a combination of the modified TNF and another anti-tumor agent, such as doxorubicin, is increased by administration of IFNγ.

STATEMENTS OF THE INVENTION

According to a first aspect, the invention provides a conjugation product of a cytokine selected from TNF and IFNγ and a ligand of CD13 receptor.

According to another aspect of the present invention there is provided a pharmaceutical composition comprising an effective amount of a conjugation product of TNF and a ligand of the CD13 receptor, and an effective amount of IFNγ.

DETAILED DESCRIPTION OF THE INVENTION

Various preferred features and embodiments of the present invention will now be described by way of non-limiting example.

Said ligand of CD13 receptor can be an antibody or a fragment thereof such as Fab, Fv, single-chain Fv, a peptide or a peptido-mimetic, namely a peptido-like molecule capable to bind the CD13 receptor, optionally containing modified, not naturally occurring amino acids.

CD13 is a trans-membrane glycoprotein of 150 kDa highly conserved in various species. It is expressed on normal cells as well as in myeloid tumor lines, in the angiogenic endothelium and is some epithelia. CD13 receptor is usually identified as "NGR" receptor. The ligands may be natural or synthetic. The term "ligand" also refers to a chemically modified ligand. The one or more binding domains of the ligand may consist of, for example, a natural ligand for the receptor, or a fragment of a natural ligand which retains binding affinity for the receptor. Synthetic ligands include the designer ligands. As used herein, the term means "designer ligands" refers to agents which are likely to bind to the receptor based on their three dimensional shape compared to that of the receptor.

The ligand is preferably a straight or cyclic peptide comprising the NGR motif, such as CNGRCVSGCAGRC (SEQ ID NO: 1), NGRAHA (SEQ ID NO: 2), GNGRG (SEQ ID NO: 3), cycloCVLNGRMEC (SEQ ID NO: 4) or cycloCNGRC (SEQ ID NO: 6), or, more preferably, the peptide CNGRC (SEQ ID NO: 5). Such ligands are described in WO98/10795 which is herein incorporated by reference. Methods of identifying ligands of CD13 receptor are disclosed in WO99/13329 which is herein incorporated by reference.

In one embodiment, the method of screening for an agent capable of binding to a CD13 receptor, the method comprising contacting the cell surface molecule with an agent and determining if said agent binds to said cell surface molecule.

As used herein, the term "agent" includes, but is not limited to, a compound, such as a test compound, which may be obtainable from or produced by any suitable source, whether natural or not. The agent may be designed or obtained from a library of compounds which may comprise peptides, as well as other compounds, such as small organic molecules and particularly new lead compounds. By way of example, the agent may be a natural substance, a biological macromolecule, or an extract made from biological materials such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptides synthesised synthetically (such as, by way of example, either using a peptide synthesizer) or by recombinant techniques or combinations thereof, a recombinant test compound, a natural or a non-natural test compound, a fusion protein or equivalent thereof and mutants, derivatives or combinations thereof.

The agent can be an amino acid sequence or a chemical derivative thereof. The substance may even be an organic compound or other chemical.

As used herein the term "peptidomimetic" is used broadly to refer to a peptide-like molecule that has the binding activity of the CD13 ligand.

Alternatively, the ligand may be derived from heavy and light chain sequences from an immunoglobulin (Ig) variable region. Such a variable region may be derived from a natural human antibody or an antibody from another species such as a rodent antibody. Alternatively the variable region may be derived from an engineered antibody such as a humanised antibody or from a phage display library from an immunised or a non-immunised animal or a mutagenised phage-display library. As a second alternative, the variable region may be derived from a single-chain variable fragment (scFv). The ligand may contain other sequences to achieve multimerisation or to act as spacers between the binding domains or which result from the insertion of restriction sites in the genes encoding the ligand, including Ig hinge sequences or novel spacers and engineered linker sequences.

The ligand may comprise, in addition to one or more immunoglobulin variable regions, all or part of an Ig heavy chain constant region and so may comprise a natural whole Ig, an engineered Ig, an engineered Ig-like molecule, a single-chain Ig or a single-chain Ig-like molecule. Alternatively, or in addition, the BP may contain one or more domains from another protein such as a toxin.

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term antibody, as used herein also includes antibody fragments either produced by the modification of whole antibodies or synthesised de novo using recombinant DNA methodologies. Antibody fragments encompassed by the use of the term "antibodies" include, but are not limited to, Fab, Fab', F(ab') 2, scFv, Fv, dsFv diabody, and Fd fragments.

If polyclonal antibodies are desired, a selected mammal (e.g., mouse, rabbit, goat, horse, etc.) is immunised with an immunogenic polypeptide bearing an epitope(s). Serum from the immunised animal is collected and treated according to known procedures. If serum containing polyclonal antibodies to an epitope contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against binding cell surface epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. As mentioned above such fragments include Fv, F(ab') and F(ab')$_2$ fragments, as well as single chain antibodies (scFv). Furthermore, the antibodies and fragments thereof may be humanised antibodies, for example as described in EP-A-239400.

The term "peptide" as used herein includes polypeptides and proteins. The term "polypeptide" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

It will be understood that polypeptide sequences for use in the invention are not limited to the particular sequences or fragments thereof but also include homologous sequences obtained from any source, for example related viral/bacterial proteins, cellular homologues and synthetic peptides, as well as variants or derivatives thereof Polypeptide sequences of the present invention also include polypeptides encoded by polynucleotides of the present invention.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has targeting activity, preferably having at least 25 to 50% of the activity as the polypeptides presented in the sequence listings, more preferably at least substantially the same activity.

Thus, sequences may be modified for use in the present invention. Typically, modifications are made that maintain the activity of the sequence. Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example truncated polypeptides that remain capable of binding to target molecule but lack functional effector domains may be useful.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy).

Conservative substitutions may be made, for example according to the Table below. Amino acids in the same block in the second column and preferably in the same line in the third column may be substituted for each other:

| ALIPHATIC | Non-polar | G A P |
|  |  | I L V |
|  | Polar - uncharged | C S T M |
|  |  | N Q |
|  | Polar - charged | D E |
|  |  | K R |
| AROMATIC |  | H F W Y |

Polypeptides of the invention also include fragments of the above mentioned polypeptides and variants thereof, including fragments of the sequences. Preferred fragments include those which include an epitope or binding domain. Suitable fragments will be at least about 5, e.g. 10, 12, 15 or 20 amino acids in length. They may also be less than 200, 100 or 50 amino acids in length. Polypeptide fragments of the proteins and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Polypeptides and conjugates of the invention are typically made by recombinant means, for example as described below. However they may also be made by synthetic means using techniques well known to skilled persons such as solid phase synthesis. Various techniques for chemical synthesising peptides are reviewed by Borgia and Fields, 2000, TibTech 18: 243-251 and described in detail in the references contained therein.

The peptide can be coupled directly to the cytokine or indirectly through a spacer, which can be a single amino acid, an amino acid sequence or an organic residue, such as 6-aminocapryl-N-hydroxysuccinimide. The coupling procedures are known to those skilled in the art and comprise genetic engineering or chemical synthesis techniques.

The peptide ligand preferably is linked to the cytokine N-terminus thus minimizing any interference in the binding of the modified cytokine to its receptor. Alternatively, the peptide can be linked to amino acid residues which are amido- or carboxylic-bonds acceptors, naturally occurring on the molecule or artificially inserted with genetic engineering techniques. The modified cytokine is preferably prepared by use of a cDNA comprising a 5'-contiguous sequence encoding the peptide.

According to a preferred embodiment, there is provided a conjugation product between TNF and the CNGRC (SEQ ID NO: 5) sequence. More preferably, the amino-terminal of TNF is linked to the CNGRC (SEQ ID NO: 5) peptide through the spacer G (glycine).

The resulting product (NGR-TNF), proved to be more active than TNF on RMA-T lymphoma animal models. Furthermore, animals treated with NGR-TNF were able to reject further tumorigenic doses of RMA-T or RMA cells. The increase in the antitumoral activity, as compared with normal TNF, could be observed in immunocompetent animals but not in immunodeficient animals. This indicates that the increase in the antitumoral activity of TNF conjugated with "NGR" peptides is due to an enhanced immune response rather than to a direct cytotoxic activity of the conjugate.

It has also been demonstrated that the in vivo immune effects induced by NGR-TNF are directly related to the CD13 receptor. It has, for example, been observed that antibody against the CD13 receptor as well as the GNGRC ligand compete with NGR-TNF in vivo, thus suggesting a mechanism of receptor targeting by NGR-TNF.

The therapeutic index of the TNF/CD13 ligand conjugates can be further improved by using a mutant form of TNF capable of selectively binding to one of the two TNF receptors, p75TNFR and p55TNFR. Said TNF mutant can be obtained by site-directed mutagenesis (5; 7).

The pharmacokinetic of the modified cytokines according to the invention can be improved by preparing polyethylene glycol derivatives, which allow to extend the plasmatic half-life of the cytokines themselves.

A further embodiment of the invention is provided by bifunctional derivatives in which the cytokines modified with the CD13 ligand are conjugated with antibodies, or their fragments, against tumoral antigens or other tumor angiogenic markers, e.g. αv integrins, metalloproteases or the vascular growth factor, or antibodies or fragments thereof directed against components of the extracellular matrix, such as anti-tenascin antibodies or anti-fibronectin EDB domain. The preparation of a fusion product between TNF and the hinge region of a mAb against the tumor-associated TAG72 antigen expressed by gastric and ovarian adenocarcinoma has recently been reported (6).

A further embodiment of the invention is provided by the tumoral pre-targeting with the biotin/avidin system. According to this approach, a ternary complex is obtained on the tumoral antigenic site, at different stages, which is formed by 1) biotinylated mAb, 2) avidin (or streptavidin) and 3) bivalent cytokine modified with the CD13 ligand and biotin. A number of papers proved that the pre-targeting approach, compared with conventional targeting with immunoconjugates, can actually increase the ratio of active molecule homed at the target to free active molecule, thus reducing the treatment toxicity (11, 10, 9, 8). This approach produced favorable results with biotinylated TNF, which was capable of inducing cytotoxicity in vitro and decreasing the tumor cells growth under conditions in which normal TNF was inactive (14, 26). The pre-targeting approach can also be carried out with a two-phase procedure by using a bispecific antibody which at the same time binds the tumoral antigen and the modified cytokine. The use of a bispecific antibody directed against a carcinoembryonic antigen and TNF has recently been described as a means for TNF tumoral pre-targeting (31).

According to a further embodiment, the invention comprises a TNF molecule conjugated to both a CD13 ligand and an antibody, or a fragment thereof (directly or indirectly via a biotin-avidin bridge), on different TNF subunits, where the antibody or its fragments are directed against an antigen expressed on tumor cells or other components of the tumor stroma, e.g. tenascin and fibronectin EDB domain. This results in a further improvement of the tumor homing properties of the modified cytokine and in the slow release of the latter in the tumor microenvironment through trimer-monomer-trimer transitions. As shown in previous works, in fact, the modified subunits of TNF conjugates can dissociate from the targeting complexes and reassociate so as to form unmodified trimeric TNF molecules, which then diffuse in the tumor microenvironment. The release of bioactive TNF has been shown to occur within 24-48 hours after targeting (21).

Peptides of the present invention may be administered therapeutically to patients. It is preferred to use peptides that do not consisting solely of naturally-occurring amino acids but which have been modified, for example to reduce immunogenicity, to increase circulatory half-life in the body of the patient, to enhance bioavailability and/or to enhance efficacy and/or specificity.

A number of approaches have been used to modify peptides for therapeutic application. One approach is to link the peptides or proteins to a variety of polymers, such as polyethylene glycol (PEG) and polypropylene glycol (PPG)—see for example U.S. Pat. Nos. 5,091,176, 5,214,131 and U.S. Pat. No. 5,264,209.

Replacement of naturally-occurring amino acids with a variety of uncoded or modified amino acids such as D-amino acids and N-methyl amino acids may also be used to modify peptides Another approach is to use bifunctional crosslinkers, such as N-succinimidyl 3-(2 pyridyldithio)propionate, succinimidyl 6-[3-(2 pyridyldithio)propionamido]hexanoate, and sulfosuccinimidyl 6-[3-(2 pyridyldithio)propionamido]hexanoate (see U.S. Pat. No. 5,580,853).

It may be desirable to use derivatives of the peptides of the invention which are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilised by a covalent modification, such as cyclization or by incorporation of gamma-lactam or other types of bridges. For example, side chains can be cyclized to the backbone so as create a L-gamma-lactam moiety on each side of the interaction site. See, generally, Hruby et al., "Applications of Synthetic Peptides," in Synthetic Peptides: A User's Guide: 259-345 (W. H. Freeman & Co. 1992). Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken. See Wood and Wetzel, 1992, Int'l J. Peptide Protein Res. 39: 533-39.

Another approach described in U.S. Pat. No. 5,891,418 is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is a sequence of four glycine residues which has four nitrogens (an $N_4$ complexation system) in the back bone that can complex to a metal ion with a coordination number of four.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data which comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation. An example of this approach is provided in U.S. Pat. No. 5,811,512.

Techniques for chemically synthesising therapeutic peptides of the invention are described in the above references and also reviewed by Borgia and Fields, 2000, TibTech 18: 243-251 and described in detail in the references contained therein.

For use in therapy, the modified cytokines of the invention will be suitably formulated in pharmaceutical preparations for the oral or parenteral administration. Formulations for the parenteral administration are preferred, and they comprise injectable solutions or suspensions and liquids for infusions. For the preparation of the parenteral forms, an effective amount of the active ingredient will be dissolved or suspended in a sterile carrier, optionally adding excipients such as solubilizers, isotonicity agents, preservatives, stabilizers, emulsifiers or dispersing agents, and it will be subsequently distributed in sealed vials or ampoules.

In more detail, conjugates of the invention, including polypeptides and polynucleotides, may preferably be combined with various components to produce compositions of the invention. Preferably the compositions are combined with a pharmaceutically acceptable carrier, diluent or excipient to produce a pharmaceutical composition (which may be for human or animal use). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association. The composition of the invention may be administered by direct injection. The composition may be formulated for parenteral, intramuscular, intravenous, subcutaneous, intraocular, oral or transdermal administration.

The composition may be formulated such that administration daily, weekly or monthly will provide the desired daily dosage. It will be appreciated that the composition may be conveniently formulated for administrated less frequently, such as every 2, 4, 6, 8, 10 or 12 hours.

Polynucleotides/vectors encoding polypeptide components may be administered directly as a naked nucleic acid construct, preferably further comprising flanking sequences homologous to the host cell genome.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since a skilled practitioner will be able to determine readily the optimum route of administration and dosage regimens for any particular patient and condition.

The preparation of cytokines in form of liposomes can improve the biological activity thereof. It has, in fact, been observed that acylation of the TNF amino groups induces an increase in its hydrophobicity without loss of biological activity in vitro. Furthermore, it has been reported that TNF bound to lipids has unaffected cytotoxicity in vitro, immunomodulating effects and reduced toxicity in vivo (12, 13).

The maximum tolerated dose of bolus TNF in humans is 218-410 $\mu g/m^2$ (32) about 10-fold lower than the effective dose in animals. Based on data from murine models it is believed that an at least 10 times higher dose is necessary to achieve anti-tumor effects in humans (15). In the first clinical study on hyperthermic isolated-limb perfusion, high response rates were obtained with the unique dose of 4 mg of TNF in combination with melphalan and interferon γ (16). Other works showed that interferon γ can be omitted and that even lower doses of TNF can be sufficient to induce a therapeutic response (17, 18). As the two cytokines exert synergistic effects on endothelial cells, their combined, selective targeting thereon is likely to result in stronger anti-tumor activity thus allowing to overcome the problems of systemic toxicity usually encountered in cancer therapy with the same cytokines used in combination. Furthermore, it is known that TNF can decrease the barrier function of the endothelial lining vessels, thus increasing their permeability to macromolecules. Taking advantage of the lower toxicity of treatment with the modified TNF molecules according to the invention, and of their tumor vessels homing properties, an alternative application is their use to increase the permeability of tumor vessels to other compounds, either for therapeutic or diagnostic purposes. For instance the modified TNF can be used to increase the tumor uptake of radiolabelled antibodies or hormones (tumor-imaging compounds) in radioimmunoscintigraphy or radioimmunotherapy of tumors. Alternatively, the uptake of chemotherapeutic drugs, immunotoxins, liposomes carrying drugs or genes, or other anticancer drugs could also be increased, so that their antitumor effects are enhanced.

Accordingly, the cytokines of the invention can be used in combined, separated or sequential preparations, also with other diagnostic or therapeutic substances, in the treatment or in the diagnosis of cancer.

Another aspect of the present invention relates to the use of a combination of the modified TNF, and IFNγ. This combination can be used in combined, separated or sequential preparations. Advantageously the combination is also with other diagnostic or therapeutic substances, in the treatment or in the diagnosis of cancer, such as doxorubicin and mephalan. Thus the present invention provides a pharmaceutical composition comprising a combination of the modified TNF and IFNγ, and optionally another tumor-diagnostic or anti-tumor therapeutic substance. Again, this combination can be used in combined, separated or sequential preparations.

In our patent application number GB 02098960, we found targeted delivery of picogram doses of cytokines enhances the penetration of chemotherapeutic drugs, providing a novel and surprising strategy for increasing the therapeutic index of chemotherapeutic drugs. Patent application number GB 02098960 is hereby incorporated by reference in its entirety. In more detail, we have found that delivery of very low doses of cytokines to tumors and the tumor-associated environment including tumor vasculature represents a new approach to avoiding negative feedback mechanisms and to preserve its ability to alter drug-penetration barriers.

The composition of the present invention may be formulated for parenteral, intramuscular, intravenous, subcutaneous, intraocular, oral or transdermal administration. In one embodiment of this aspect of the present invention, a conjugate of the present invention may be administered at a dose of from in the range of 0.5 to 500 ng/kg, preferably in the range of 1 to 50 ng/kg, more preferably in the range of 5 to 15 ng/kg.

In an alternative embodiment of this aspect of the invention there is provided a pharmaceutical composition comprising a conjugate of the present invention in combination with IFNγ, wherein the conjugate is present in an amount such that the conjugate or a metabolite thereof is provided to the blood plasma of the subject to be treated in an amount of no greater than about 35,000 ng/day, preferably about 3,500 ng/day, more preferably about 1,000 ng/day.

The above dosage relate to a dosage for a 70 kg subject. A person skilled in the art would readily be able to modify the recited dosage for a subject having as mass other than 70 kg.

The routes of administration and dosage regimens described are intended only as a guide since a skilled practitioner will be able to determine readily the optimum route of administration and dosage regimens for any particular patient and condition.

Another aspect of the invention regards the cDNA encoding for the conjugated cytokines herein disclosed, which can be prepared from the cytokines cDNA by addition of a 5'- or 3'-contiguous DNA sequence encoding for the CD13 ligand, preferably for the homing peptides described above. The combined cDNA can be used as such or after insertion in vectors for gene therapy. The preparation and therapeutic applications of suitable vectors is disclosed in (19), which is hereby incorporated by reference.

Polynucleotides for use in the invention comprise nucleic acid sequences encoding the polypeptide conjugate of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for certain cells may also be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Vectors and polynucleotides of the invention may be introduced into host cells for the purpose of replicating the vectors/polynucleotides and/or expressing the proteins of the invention encoded by the polynucleotides of the invention. Although the proteins of the invention may be produced using prokaryotic cells as host cells, it is preferred to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Host cells comprising polynucleotides of the invention may be used to express conjugates of the invention. Host cells may be cultured under suitable conditions which allow expression of the polypeptides and conjugates of the invention. Expression of the products of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Conjugates of the invention can be extracted from host cells by a variety of techniques known in the art, including enzymatic, chemical and/or osmotic lysis and physical disruption.

5 Animals/group were treated with a single dose of TNF or NGR-TNF (i.p.), 10 days after tumor implantation. Tumor area values at day 14 as a function of the dose (b) and the loss of weight after treatment (mean of days 11 and 12) (d), were interpolated from logarithmic curves. The anti-tumor effects induced by 1 µg or 9 µg of NGR-TNF at day 14 were greater than those induced by comparable amounts of TNF (P=0.024 and P=0.032, respectively), while the loss of weight after these treatments was similar. The arrows indicate extrapolated doses of TNF and NGR-TNF that induce comparable effects.

Figure 2A:
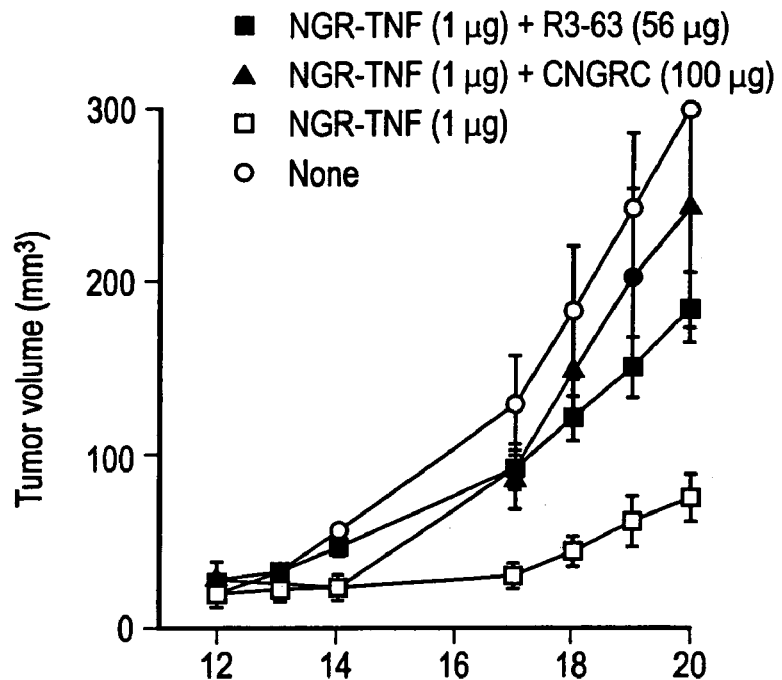

FIG. 2: Effect of mAb R3-63 and CNGRC on the anti-tumor activity of NGR-TNF (a) and TNF (b).

MAb R3-63 or CNGRC (SEQ ID NO: 5) were mixed with NGR-TNF or TNF and administered to RMA-T tumor bearing animals, 12 days after tumor implantation (n=5 animals/group). In a separate experiment (c) TNF and NGR-TNF were coadministered with CNGRC (SEQ ID NO: 5) or CARAC SEQ ID NO: 19) (a control peptide) to animals bearing 11-day old tumors (n=5). The anti-tumor effect of 1 µg of NGR-TNF was stronger than that of 9 µg of TNF (P=0.009, t-test at day 20) and was significantly inhibited by CNGRC (SEQ ID NO: 5) (P=0.035) and by mAb R3-63 (P=0.011).

Figure 3A:
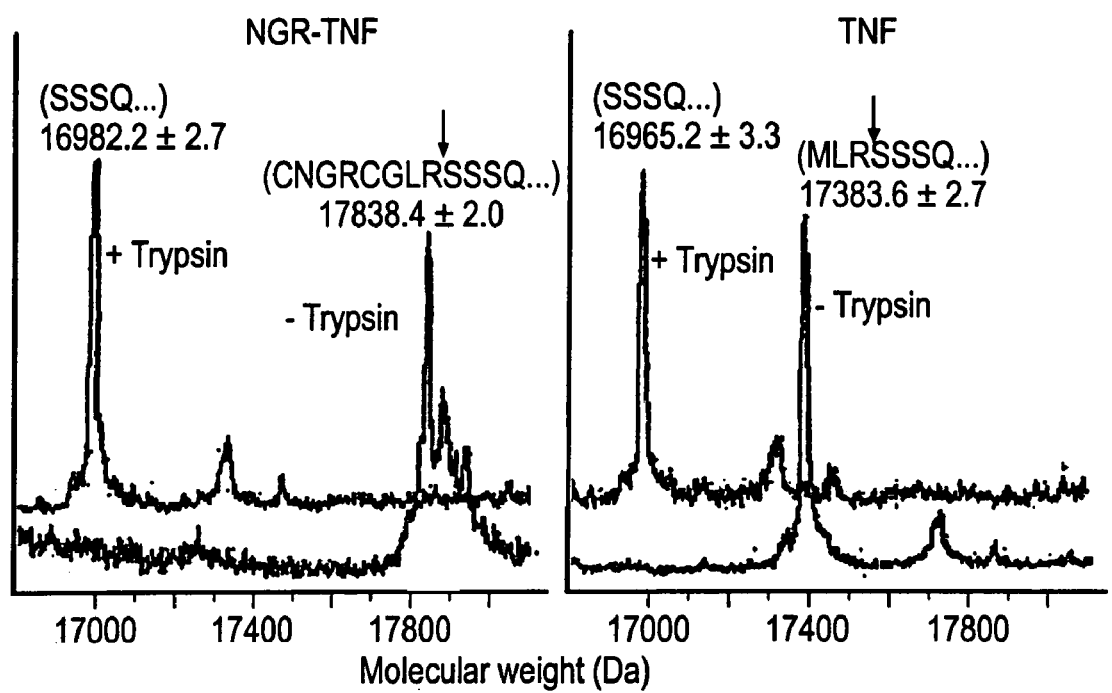

FIG. 3: Effect of limited tryptic digestion of NGR-TNF and TNF on their mass (a) and anti-tumor activity (b).

Trypsin-agarose was prepared by coupling 1 mg of trypsin to 1 ml of Activated CH Sepharose (Pharmacia-Upjohn), according to the manufacturer's instructions. NGR-TNF and TNF (170 µg each in 300 µl of 0.15 M sodium chloride, 0.05 M sodium phosphate, pH 7.3) were mixed with 15 µl of resin suspension (1:4) or buffer alone and rotated end-over-end at 37° C. for the indicated time. The four products were filtered through a 0.22 µm Spin-X device (Costar, Cambridge, Mass.) and stored at −20° C. until use. (a) Electrospray mass spectrometry analysis. The molecular mass values and the corresponding products (N-terminal sequences) are indicated on each peak. The arrows on the sequences indicate the site of cleavage. (b) Effect of 1 or 3 µg of NGR-TNF and TNF, incubated without (upper panels) or with (lower panels) trypsin, on the growth of RMA-T tumors and animal weight (mean±SE of groups treated with 1 and 3 µg doses). Animals were treated 13 days after tumor implantation (n=5 animals/group).

FIG. 4: SDS-PAGE and anti-tumor activity of human NGR-TNF before and after denaturation/refolding.

SDS-PAGE under non reducing conditions (A) of human TNF (a), NGR-TNF before (b) and after (c) the denaturation/refolding process described in Example V.

Effect of TNF and non-refolded NGR-TNF on the growth of RMA-T lymphomas (B) and on body weight (C). Effect of human TNF (D) and refolded NGR-TNF (consisting of >95% trimers with intra-chain disulfides) (E) on the tumor growth. Animals (15 or 5 mice/group as indicated in each panel) were treated with one i.p. dose of TNF or NGR-TNF, 10 days after tumor implantation.

FIG. 5: Effect of a neutralising anti-mIFNγ antibody (AN18) on the antitumor activity of NGR-mTNF and doxorubicin on B16F1 tumors in C57BL6 mice.

Figure 6:
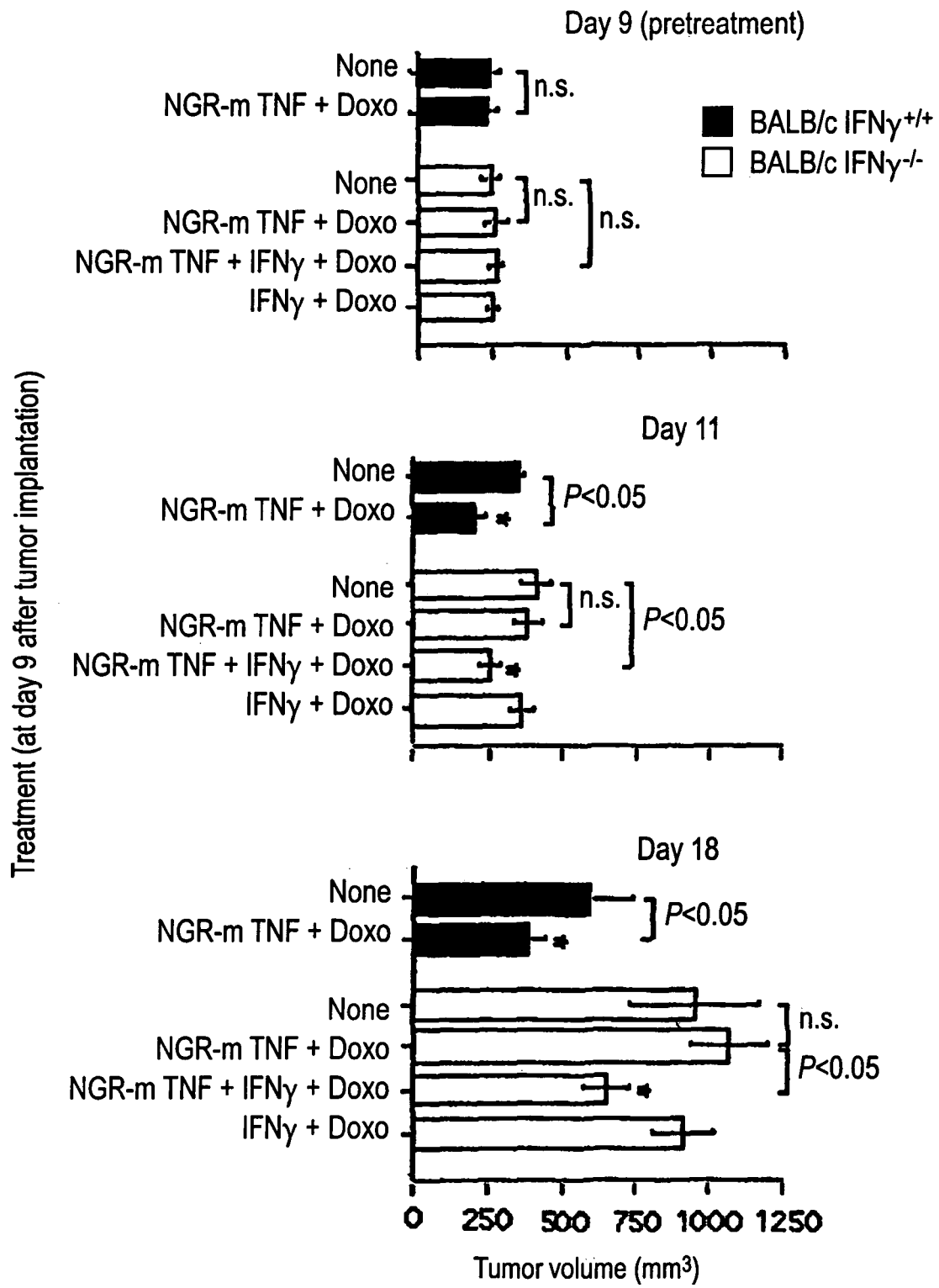

FIG. 6: Effect of NGR-TNF and doxorubicin in IFN knock out mice.

Figure 7:
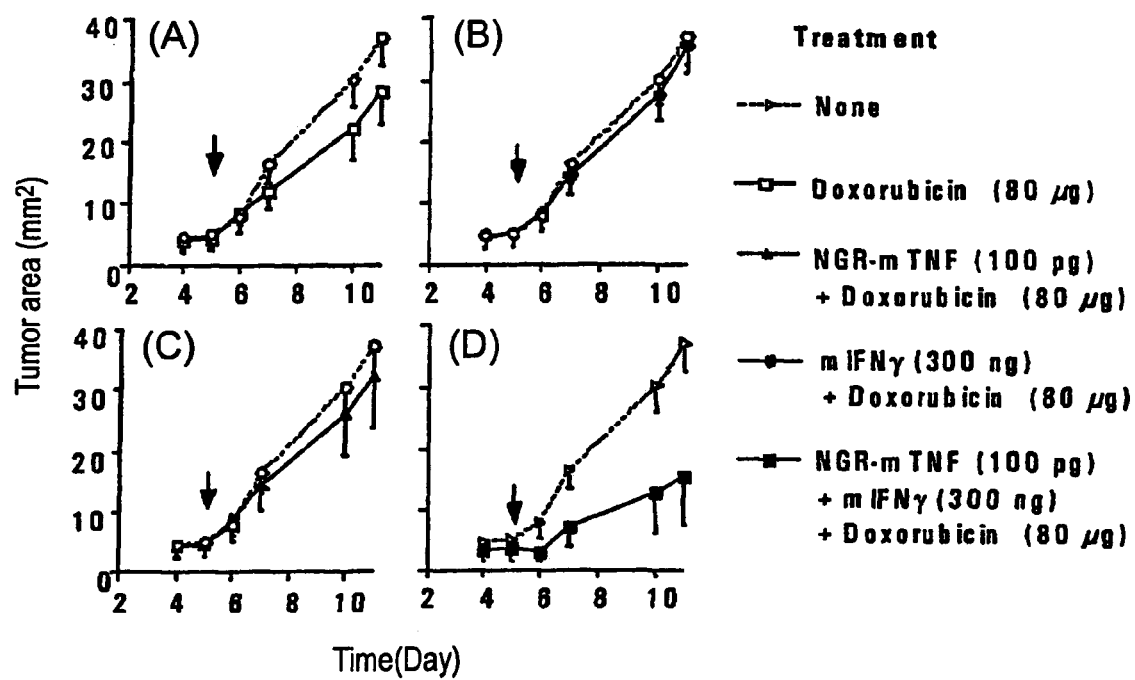

FIG. 7: Effect of NGR-mTNF, mIFNγ and doxorubicin (alon or in combinantion) on B16F1 tumors in nude mice.

Figure 8:
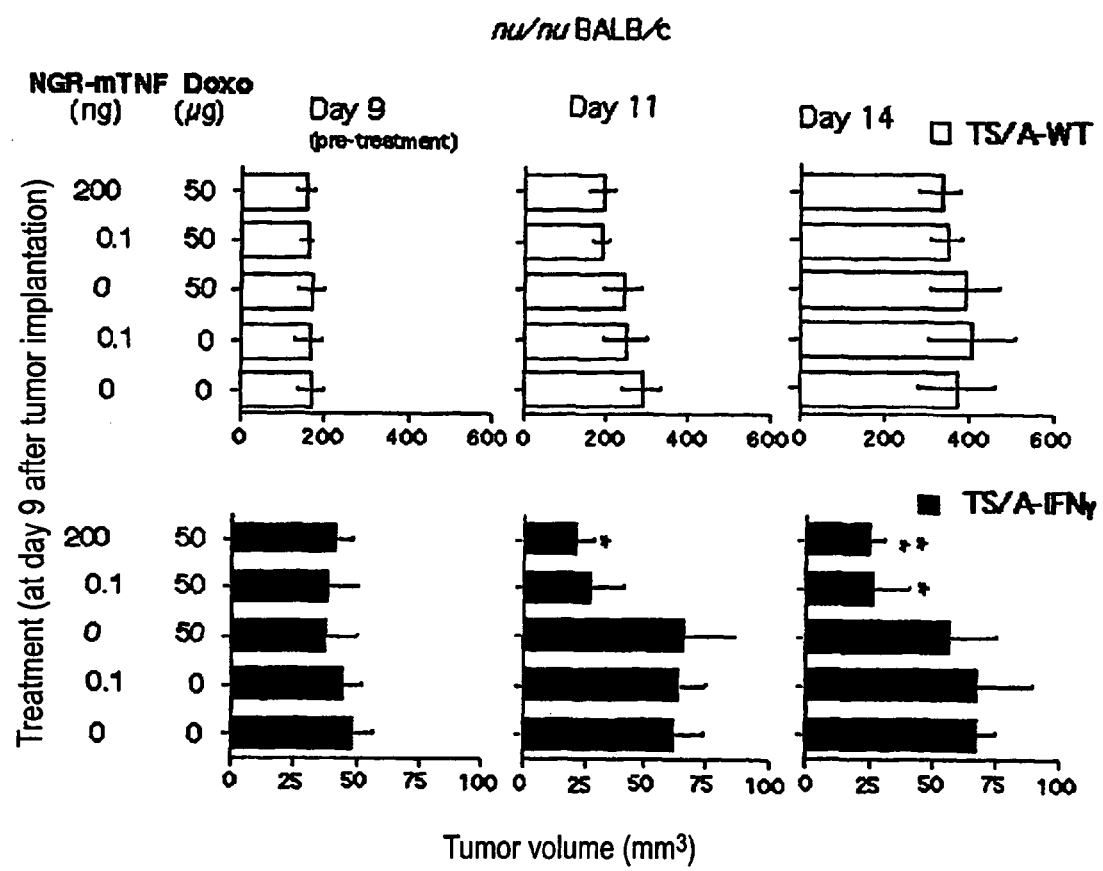

FIG. 8: Effect of NGR-TNF and doxorubicin in nude mice

Figure 9:
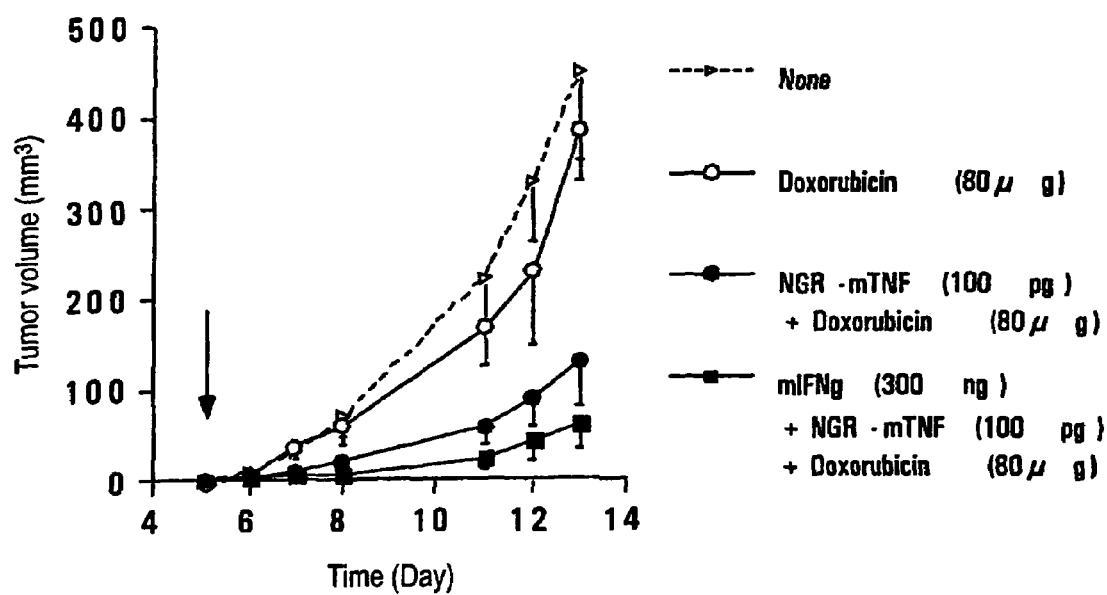

FIG. 9: Effect of NGR-mTNF, mIFNγ and doxorubicin on B16F1 tumors in immunocompetent mice (C57BL6).

Figure 10:
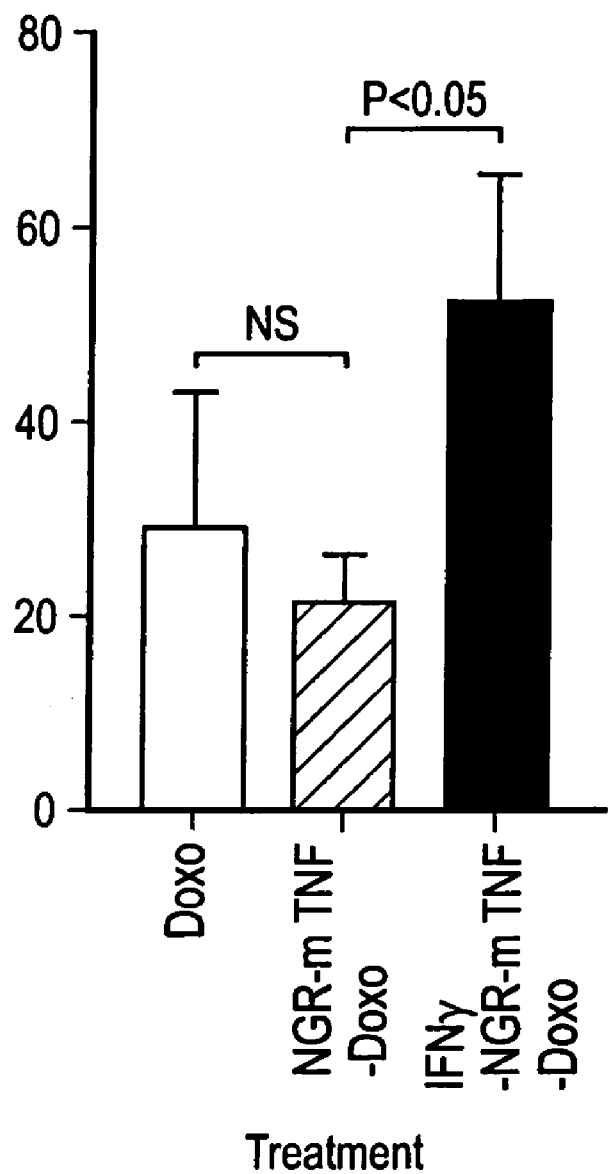

FIG. 10: IFN increase the penetration of doxorubicin in tumours when combined with NGR-TNF in IFN knock out animals.

The following examples further illustrate the invention.

EXAMPLE I

Preparation of Murine TNF and NGR-TNF

Murine recombinant TNF and Cys-Asn-Gly-Arg-Cys-Gly-TNF (NGR-TNF) (SEQ ID NO: 18) were produced by cytoplasmic cDNA expression in *E.coli*. The cDNA coding for murine Met-TNF$_{1-156}$ (20) was prepared by reverse transcriptase-polymerase chain reaction (RT-PCR) on mRNA isolated from lipopolysaccharide-stimulated murine RAW-264.7 monocyte-macrophage cells, using

```
5'-CTGGATCCTCACAGAGCAATGACTCCAAAG-3' (SEQ ID NO:7)
and

5'-TGCCTCACATATGCTCAGATCATCTTCTC-3', (SEQ ID NO:8)
as 3' and 5' primers.
```

The amplified fragment was digested with Nde I and Bam HI (New England Biolabs, Beverley, Mass.) and cloned in pET-11b (Novagen, Madison, Wis.), previously digested with the same enzymes (pTNF).

The cDNA coding for Cys-Asn-Gly-Arg-Cys-Gly-TNF$_{1-56}$ (SEQ ID NO: 18) was amplified by PCR on pTNF, using 5'-GCAGATCATATGTGCAACGGCCGTTGCG-GCCTCAGATCATCTTCTC-3' (SEQ ID NO: 9) as 5' primer, and the above 3' primer. The amplified fragment was digested and cloned in pET-11b as described above and used to transform BL21(DE3) *E.coli* cells (Novagen). The expression of TNF and NGR-TNF was induced with isopropyl-β-D-thiogalactoside, according to the pET11b manufacturer's instruction. Soluble TNF and NGR-TNF were recovered from two-liter cultures by bacterial sonication in 2 mM ethylenediaminetetracetic acid, 20 mM Tris-HCl, pH 8.0, followed by centrifugation (15000×g, 20 min, 4° C.). Both extracts were mixed with ammonium sulfate (25% of saturation), left for 1 h at 4° C., and further centrifuged, as above. The ammonium sulfate in the supernatants was then brought to 65% of saturation, left at 4° C. for 24 h and further centrifuged. Each pellet was dissolved in 200 ml of 1 M ammonium sulfate, 50 mM Tris-HCl, pH 8.0, and purified by hydrophobic interaction chromatography on Phenyl-Sepharose 6 Fast Flow (Pharmacia-Upjohn) (gradient elution, buffer A: 50 mM sodium phosphate, pH 8.0, containing 1 M ammonium sulfate; buffer B: 20% glycerol, 5% methanol, 50 mM sodium phosphate, pH 8.0). Fractions containing TNF immunoreactive material (by western blotting) were pooled, dialyzed against 2 mM ethylenediaminetetracetic acid, 20 mM Tris-HCl, pH 8.0 and further purified by ion exchange chromatography on DEAE-Sepharose Fast Flow (Pharmacia-Upjohn) (gradient elution, buffer A: 20 mM Tris-HCl, pH 8.0; buffer B: 1 M sodium chloride, 20 mM Tris-HCl, pH 8.0). Fractions containing TNF-immunoreactivity were pooled and purified by gel filtration chromatography on Sephacryl-S-300 HR (Pharmacia-Upjohn), pre-equilibrated and eluted with 150 mM sodium chloride, 50 mM sodium phosphate buffer, pH 7.3 (PBS). Fractions corresponding to 40000-50000 Mr products were pooled, aliquoted and stored frozen at −20° C. All solutions employed in the chromatographic steps were prepared with sterile and endotoxin-free water (Salf, Bergamo, Italy). The final yields were 45 mg of TNF and 34.5 mg NGR-TNF.

The molecular weight of purified TNF and NGR-TNF was measured by electrospray mass spectrometry. The protein content was measured using a commercial protein assay kit (Pierce, Rockford, Ill.). Endotoxin content of NGR-TNF and TNF was 0.75 units/µg and 1.38 units/µg, respectively, as measured by the quantitative chromogenic Lymulus Amoebocyte Lysate (LAL) test (BioWhittaker).

Sodium dodecylsulfate-polyacrylamide gel electrophoresis (SDS-PAGE) and western blot analysis were carried out using 12.5 or 15% polyacrylamide gels, by standard procedures.

A small amount of TNF and NGR-TNF was further purified by affinity chromatography on soluble p55-TNF receptor (sTNF-R1)-Sepharose as follows: 5 mg of recombinant sTNF-R1 were prepared as described (22) and coupled to 2 ml of Activated-CH-Sepharose (Pharmacia), according to the manufacturer's instruction. Two separate columns (one ml each), were washed extensively with sterile and endotoxin-free solutions, loaded with purified TNF or NGR-TNF in PBS and desorbed by gradient elution (1 h, buffer A: PBS; buffer B: 0.5 M sodium chloride, 0.2 M glycine-HCl). The TNF-antigen containing fractions were neutralized and dialyzed against sterile physiological solution. Endotoxin-free human serum albumin was added before dialysis (0.5 mg/ml) to prevent protein adsorption on membranes. The TNF content in each fraction was measured by ELISA and cytolytic assay.

Non reducing SDS-PAGE of TNF showed a single band of 17-18 kDa, as expected for monomeric TNF (not shown). At variance, non reducing SDS-PAGE and western blot analysis of NGR-TNF showed different immunoreactive forms of 18, 36 and 50 kDa likely corresponding to monomers, dimers and trimers. Under reducing conditions most of the 50 and 36 kDa bands were converted into the 18 kDa form, pointing to the presence of NGR-TNF molecules with interchain disulfide bridges. The 18 kDa band accounted to about ⅔ of the total material, whereas the 36 kDa accounted for most of the remaining part. These electrophoretic patterns suggest that NGR-TNF was a mixture of trimers made up by three monomeric subunits with correct intra-chain disulfides (at least 50%) and the remaining part mostly by trimers with one or more interchain disulfides. The 36 kDa band still observed by reducing SDS-PAGE suggests that NGR-TNF contained also an irreversible denatured dimer (about 10% of total).

The molecular mass of TNF and NGR-TNF monomers were 17386.1±2.0 Da and 17843.7±2.5 Da, respectively, by electrospray mass spectrometry. These values correspond very well to the mass expected for Met-TNF$_{1-156}$ (17386.7 Da) and for CNGRCG-TNF$_{1-156}$ (17844.2 Da).

EXAMPLE II

In Vitro Cytotoxic Activity of Murine TNF and NGR-TNF

The bioactivity of TNF and NGR-TNF was estimated by standard cytolytic assay based on L-M mouse fibroblasts (ATCC CCL1.2) as described (23). The cytolytic activity of TNF and NGR-TNF on RMA-T cells was tested in the presence of 30 ng/ml actinomycin D. Each sample was analyzed in duplicate, at three different dilutions. The results are expressed as mean±SD of two-three independent assays.

The in vitro cytotoxic activity of TNF and NGR-TNF was $(1.2\pm0.14)\times10^8$ units/mg and $(1.8\pm0.7)\times10^8$ units/mg, respectively, by standard cytolytic assay with L-M cells. These results indicate that the CNGRCG (SEQ ID NO: 18) moieties in the NGR-TNF molecule does not prevent folding, oligomerization and binding to TNF receptors.

In a previous study we showed that RMA-T cells can be killed by TNF in the presence of 30 ng/ml actinomycin D, whereas in the absence of transcription inhibitors these cells are resistant to TNF, even after several days of incubation. The in vitro cytotoxic activity of NGR-TNF on RMA-T cells in the presence of actinomycin D was $(1.4\pm0.8)\times10^8$ units/mg, as measured using TNF $((1.2\pm0.14)\times10^8$ units/mg) as a standard. Thus, the cytotoxic activities of NGR-TNF and TNF were similar both on L-M and RMA-T cells.

EXAMPLE III

Characterization of the Therapeutic and Toxic Activity of Murine TNF and NGR-TNF The Rauscher virus-induced RMA lymphoma of C57BL/6 origin, were maintained in vitro in RPMI 1640, 5% foetal bovine serum (FBS), 100 U/ml penicillin, 100 µg/ml streptomycin, 0.25 µg/ml amphotericin B, 2 mM glutamine and 50 µM 2-mercaptoethanol. RMA-T was derived from the RMA cell line by transfection with a construct encoding the Thy 1.1 allele and cultured as described (14).

B16F1 melanoma cells were cultured in RPMI 1640, 5% FBS, 100 U/ml penicillin, 100 µg/ml streptomycin, 0.25 µg/ml amphotericin B, 2 mM glutamine, 1% MEM non essential amino acid (BioWhittaker Europe, Verviers, Belgium).

In vivo studies on animal models were approved by the Ethical Committee of the San Raffaele H Scientific Institute and performed according to the prescribed guidelines. C57BL/6 (Charles River Laboratories, Calco, Italy) (16-18 g) were challenged with $5\times10^4$ RMA-T or B16F1 living cells, respectively, s.c. in the left flank. Ten-twelve days after tumor implantation, mice were treated, i.p., with 250 µl TNF or NGR-TNF solutions, diluted with endotoxin-free 0.9% sodium chloride. Preliminary experiments showed that the anti-tumor activity was not changed by the addition of human serum albumin to TNF and NGR-TNF solutions, as a carrier. Each experiment was carried out with 5 mice per group. The tumor growth was monitored daily by measuring the tumor size with calipers. The tumor area was estimated by calculating $r_1 \times r_2$, whereas tumor volume was estimated by calculating $r_1 \times r_2 \times r_3 \times 4/3$, where $r_1$ and $r_2$ are the longitudinal and lateral radii, and $r_3$ is the thickness of tumors protruding from the surface of normal skin. Animals were killed before the tumor reached 1.0-1.3 cm diameter. Tumor sizes are shown as mean±SE (5-10 animals per group as indicated in the figure legends) and compared by t-test.

The anti-tumor activity and toxicity of NGR-TNF were compared to those of TNF using the RMA-T lymphoma and the B16F1 melanoma models in C57BL6 mice. Since the RMA-T model has been previously characterized and used to study the anti-tumor activity of TNF with different targeting protocols (26) we decided to use this model also in this study.

Murine TNF administered to animals bearing established s.c. RMA-T tumors, causes 24 h later a reduction in the tumor mass and haemorragic necrosis in the central part of the tumor, followed by a significant growth delay for few days (26). A single treatment with TNF does not induce complete regression of this tumor, even at doses close to the LD50, as living cells remaining around the necrotic area restart to grow few days after treatment.

Figure 1A:
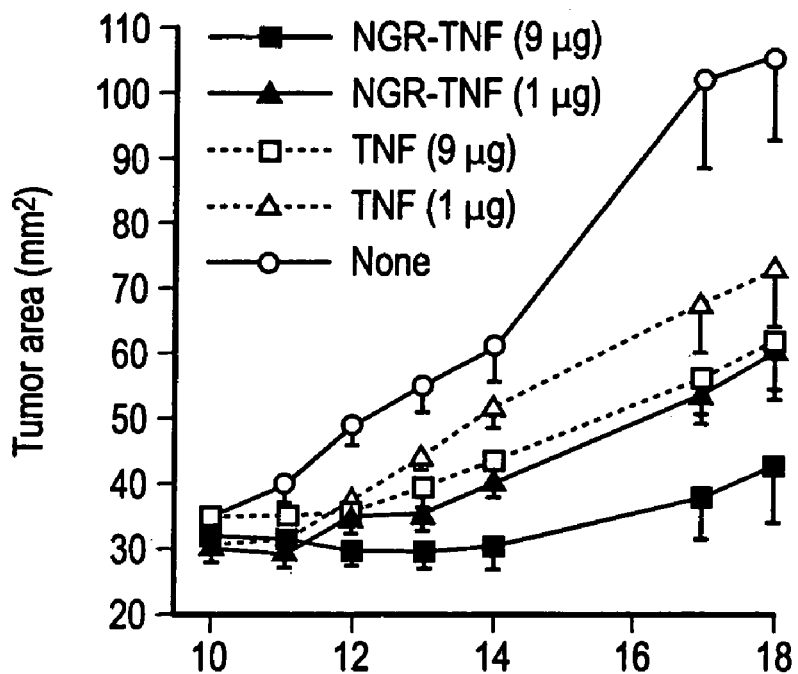
FIG. 1: Effect of TNF and NGR-TNF on the growth of RMA-T lymphomas (a and b) and on the animal weight (c and d).
Figure 1B:
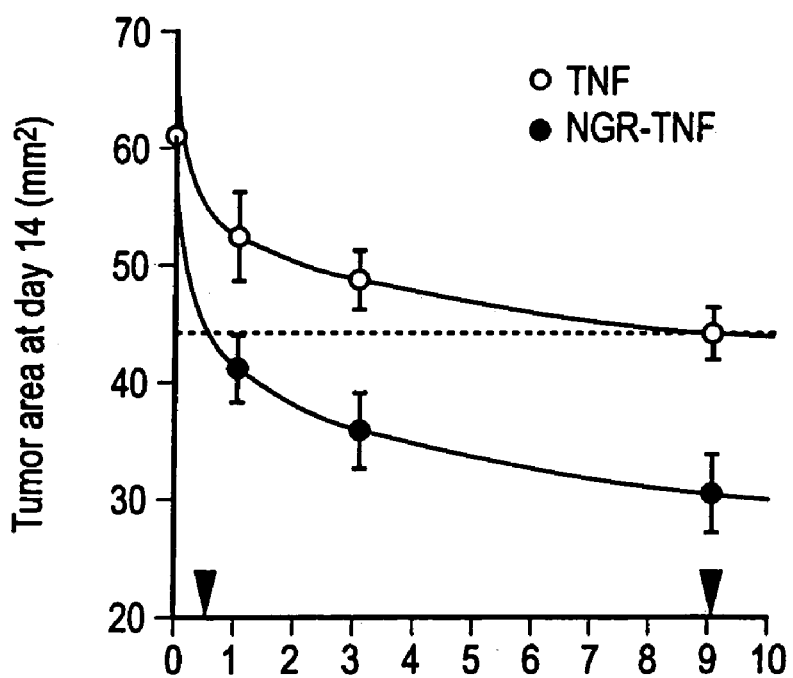
Figure 1C:
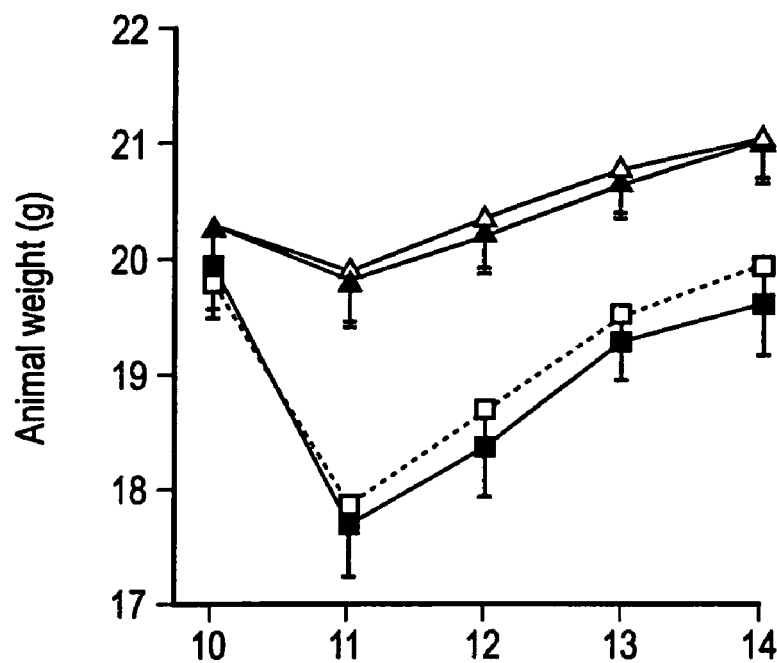
Figure 1D:
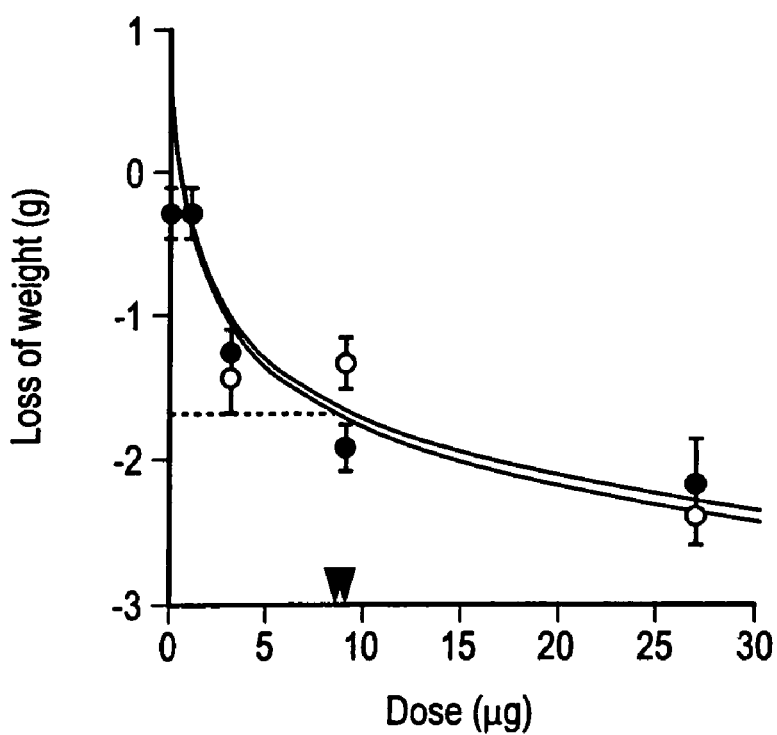

In a first set of experiments we investigated the effect of various doses (i.p.) of TNF or NGR-TNF on animal survival. To avoid excessive suffering, the animals were killed when the tumor diameter was greater than 1-1.3 cm. The lethality of TNF and NGR-TNF, 3 days after treatment, was similar (LD50, 60 μg and 45 μg, respectively) whereas their anti-tumor activity was markedly different (Table 1).

comparable to that of 1 μg of TNF (FIG. 1c). When we interpolated the data with a logarithmic curve in a dose-response plot we found that the therapeutic effect of 9 μg of TNF at day 14 can be obtained with as little as 0.6 μg of NGR-TNF (FIG. 1b). In contrast, 8.5 μg were necessary to induce a comparable toxic effect (FIG. 1d). Thus, the calculated efficacy/toxicity ratio of NGR-TNF under these conditions is 14 times greater than that of TNF.

Similar results were obtained with the B16F1 melanoma model. Treatment with 1 μg of NGR-TNF at day 11 and day 17, induced an anti-tumor response at day 19 greater than that obtained with 4 μg of TNF and similar to that obtained with 12 μg of TNF (data not shown). In contrast, the loss of weight caused by 1 μg of NGR-TNF was markedly lower than that caused by 4 and 12 μg of TNF. Treatment with 12 μg of NGR-TNF caused an even stronger anti-tumor effect, while the toxic effect was similar to that of 12 μg of TNF.

When a third injection was done on day 19 some animal deaths occurred 1-2 days later in all groups (2 out of 5 in the group treated with saline and 12 μg of NGR-TNF and 1 out of 5 in the remaining groups). Of note, one animal treated with 12 μg of NGR-TNF completely rejected the tumor. When this animal was challenged with a second tumorigenic dose of

TABLE 1

Survival of mice with RMA-T lymphoma treated with murine TNF or NGR-TNF

| Treatment | Animals (n) | Dose (μg) | Survival (%)[a] after treatment | | | | | | | |
|---|---|---|---|---|---|---|---|---|---|---|
| | | | Day 3 | Day 7 | Day 14 | Day 21 | Day 30 | Day 38 (2$^{nd}$ ch)[b] | Day 62 (3° ch.)[b] | Day 92 |
| None | 18 | 0 | 100 | 0 | | | | | | |
| TNF | 4 | 1 | 100 | 20 | 0 | | | | | |
| | 9 | 3 | 100 | 55 | 0 | | | | | |
| | 9 | 9 | 100 | 55 | 22 | 11 | 0 | | | |
| | 14 | 27 | 100 | 57 | 14 | 7 | 0 | | | |
| | 9 | 54 | 55 | 55 | 0 | | | | | |
| | 9 | 108 | 0 | | | | | | | |
| NGR-TNF | 10 | 1 | 100 | 70 | 10 | 10 | 10 | 0 | | |
| | 10 | 3 | 100 | 80 | 20 | 20 | 20 | 0 | | |
| | 9 | 9 | 100 | 88 | 55 | 22 | 11 | 11 | 11 | |
| | 13 | 27 | 100 | 85 | 30 | 23 | 15 | 15 | 15 | 11 |
| | 9 | 54 | 33 | 33 | 0 | | | | | 15 |
| | 9 | 108 | 0 | | | | | | | |

[a] Animals with tumor were treated with TNF or NGR-TNF (i.p.) 10 days after tumor implant. Animals were killed when the tumor diameter exceeded 1-1.3 cm.
[b] Surviving animals were re-challenged with 50,000 RMA-T cells (second challenge) or 50,000 RMA (third) at the indicated time. Tumorigenicity of injected cells was monitored at each time with the 5 normal animals. All control animals developed a tumor within 10 days. (data not shown).

For instance, 1 or 3 μg of NGR-TNF delayed tumor growth more efficiently then 27 μg of TNF, indicating that NGR-TNF was at least one order of magnitude more active. Interestingly, some animals were cured with doses of NGR-TNF lower than the LD50, whereas no animals at all were cured with TNF. Cured animals rejected further challenges with tumorigenic doses of either RMA-T or wild-type RMA cells, suggesting that a single treatment with NGR-TNF was able to induce protective immunity. It is noteworthy that increasing the dose of TNF or NGR-TNF above 9-27 μg markedly increased the toxicity and poorly or not the therapeutic activity.

The loss of weight consequent to TNF treatment is a well known sign of systemic toxicity (26). Thus, to further compare the efficacy/toxicity ratio of TNF and NGR-TNF we monitored the tumor growth and the animal weight after treatment. The effect of 1 μg of NGR-TNF on the tumor growth was similar or higher than that of 9 μg of TNF (FIG. 1a), while the loss of weight one-two days after treatment was B16F1 cells, a palpable tumor developed after 18 days, while control animals developed a tumor within 6-7 days.

These results, altogether, suggest that the efficacy of NGR-TNF in inhibiting the tumor growth is 10-15 times greater than that of TNF whereas the toxicity is similar. Moreover, NGR-TNF can induce protective immune responses more efficiently than TNF.

EXAMPLE IV

Mechanism of Action of NGR-TNF

Anti-mouse CD13 mAb R3-63 purified from ascitic fluids by protein-G Sepharose chromatography (Pharmacia-Upjohn, Uppsala, Sweden), and dialyzed against 0.9% sodium chloride.

Rabbit polyclonal antiserum was purchased from Primm srl (Milan, Italy) and purified by affinity chromatography on protein-A-Sepharose (Pharmacia-Upjohn). CNGRC (SEQ ID NO: 5) and CARAC (SEQ ID NO: 19) peptides were prepared as described previously (28).

Figure 2B:
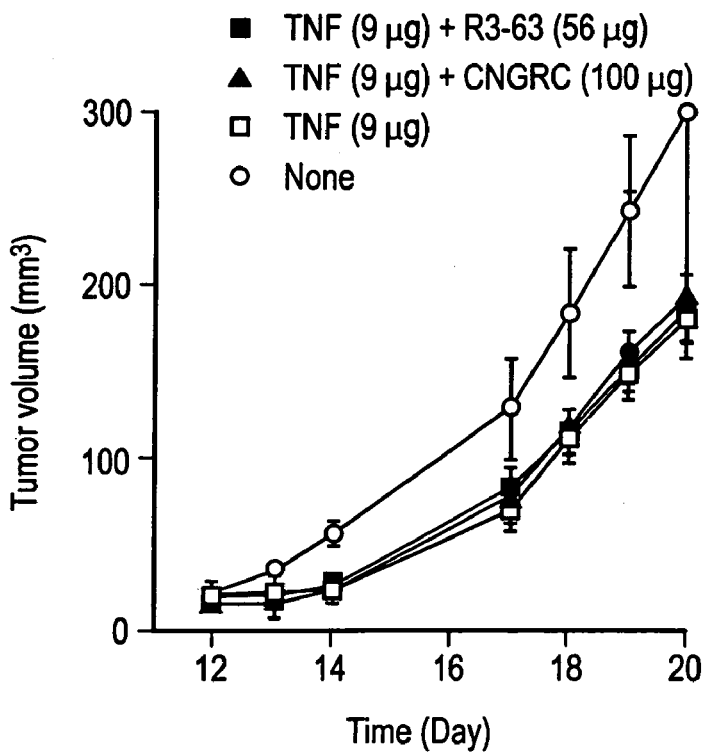
Figure 2C:
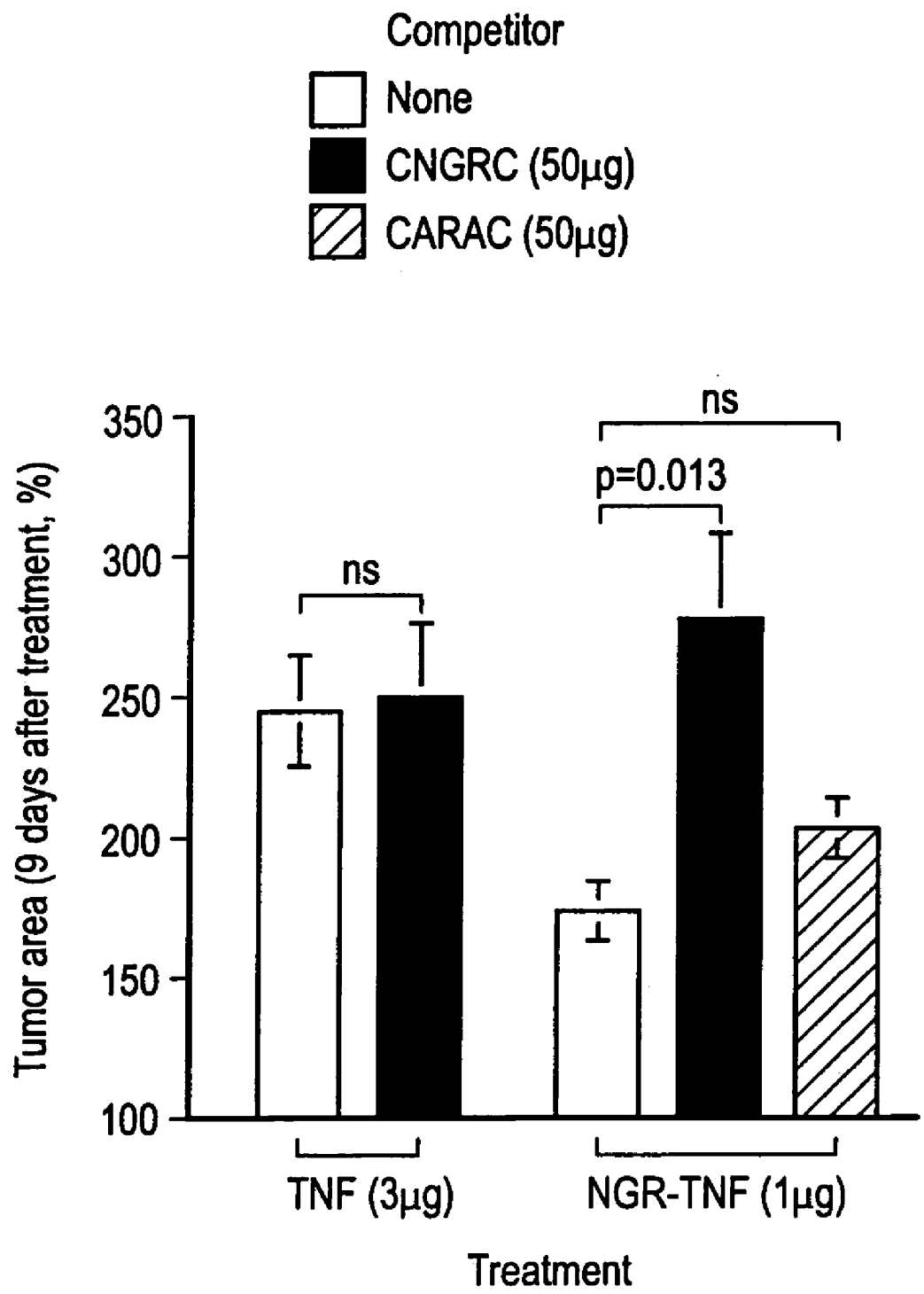

To provide evidence that the improved activity of NGR-TNF is dependent on tumor targeting via the NGR moiety we have investigated whether the in vivo activity of NGR-TNF can be partially competed by CNGRC (SEQ ID NO: 5). To this end we have administered NGR-TNF (1 μg) to RMA-T tumor bearing mice, with or without a molar excess of CNGRC (SEQ ID NO: 5). In parallel, other animals were treated with TNF (3 or 9 μg), again with or without CNGRC (SEQ ID NO: 5). As expected, CNGRC (SEQ ID NO: 5) decreased significantly the anti-tumor activity of NGR-TNF (FIG. 2a) but not that of TNF (FIG. 2b). At variance, a control peptide (CARAC) (SEQ ID NO: 19) was unable to cause significant decrease of NGR-TNF activity (FIG. 2c). These results suggest that CNGRC (SEQ ID NO: 5) competes for the binding of NGR-TNF to a CNGRC (SEQ ID NO: 5) receptor, and support the hypothesis of a targeting mechanism for the improved activity. Of note, CNGRC (SEQ ID NO: 5) was unable to decrease the in vitro cytotoxic activity of NGR-TNF (data not shown).

Since it has been recently reported that aminopeptidase N (CD13) is a receptor for CNGRC (SEQ ID NO: 5) peptides, we then investigated the contribute of this receptor in the targeting mechanism of NGR-TNF. To this end, we studied the effect of an anti-CD13 mAb (R3-63) on the anti-tumor activity of NGR-TNF and TNF. MAb R3-63 significantly inhibited the anti-tumor activity of NGR-TNF (FIG. 2a) but not that of TNF (FIG. 2b) indicating that CD13 is indeed critically involved in the anti-tumor activity of NGR-TNF. No expression of CD13 on RMA-T cell surface was observed by FACS analysis of cultured cells with mAb R3-63 (not shown), suggesting that other cells were recognized by the antibody in vivo.

Although these data indicate that CD13 is an important receptor for NGR-TNF, we cannot entirely exclude that binding to other not yet identified NGR receptors also contribute, albeit to a lower extent, to the targeting mechanism.

Preliminary experiments of partial proteolysis showed that the Arg-Ser bond in the N-terminal segment of TNF (residues 2-3) is very sensitive to trypsin, whereas the rest of the molecule is much more resistant. Thus, to provide further evidence that the improved activity of NGR-TNF is related to its NGR moiety, we tried to cleave out the NGR domain from the N-terminal region of the mutein by partial digestion with immobilized trypsin. This treatment converted both NGR-TNF and TNF into a molecule corresponding to the TNF3-156 fragment (expected mass 16986.2 Da; see FIG. 3a for measured mass and expected sequences).

Figure 3B:
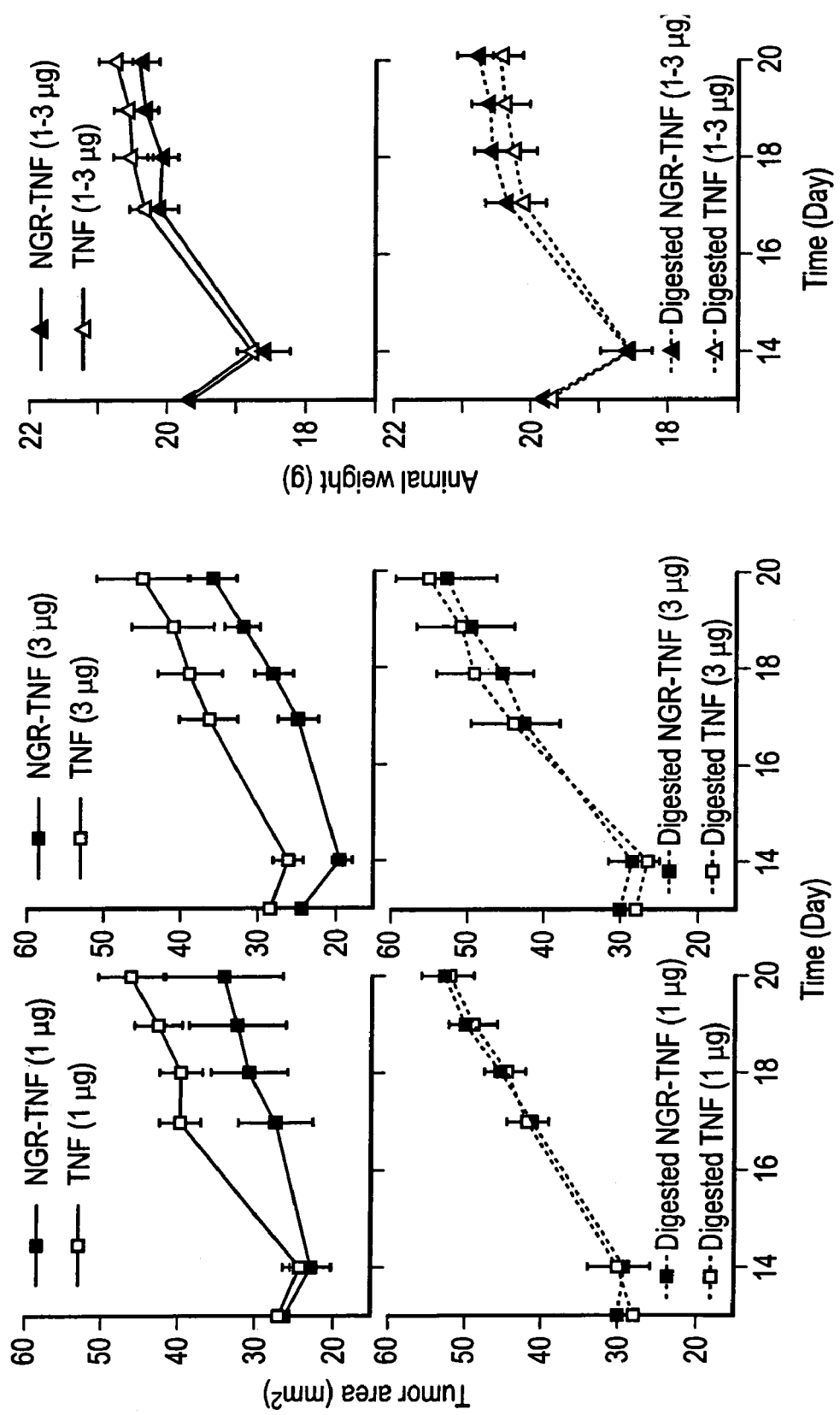

While digestion did not decrease the in vitro cytolytic activity of NGR-TNF on L-M cells $(2.3\pm1.4)\times10^8$ U/mg) its in vivo anti-tumor activity was decreased to the level of TNF (FIG. 3b). Of note, the toxicity of NGR-TNF and TNF were similar both before and after digestion, as judged from animal weight loss one day after treatment (FIG. 3b, right panel), suggesting that the NGR-dependent targeting mechanism does not alters the toxicity.

EXAMPLE V

Preparation and Characterization of Human TNF and NGR-TNF

Human recombinant TNF and NGR-TNF (consisting of human TNF1-157 fused with the C terminus of CNGRCG (SEQ ID NO: 18)) were prepared by recombinant DNA technology and purified essentially as described for murine TNF and NGR-TNF. The cDNA coding for human NGR-TNF was prepared by PCR on plasmid pET11b/hTNF containing the hTNF coding sequence (33), using the following primers:

```
NGR-hTNF/1 (sense):
5'A TAT CAT ATG TGC AAC GGC CGT TGC   (SEQ ID NO:10)
GGC GTC AGA TCA TCdT TCT CG 3'.

NGR-hTNF/2 (antisense):
5' TCA GGA TCC TCA CAG GGC AAT GAT   (SEQ ID NO:11)
CCC AAA GTA GAC 3'.
```

The amplified fragment was digested and cloned in pET-11b (Nde I/BamH I) and used to transform BL21(DE3) E.coli cells (Novagen). The expression of NGR-hTNF was induced with isopropyl-β-D-thiogalactoside, according to the pET11b manufacturer's instruction. Soluble NGR-TNF was recovered from two-liter cultures by bacterial sonication in 2 mM ethylenediaminetetracetic acid, 20 mM Tris-HCl, pH 8.0, followed by centrifugation (15000×g, 20 min, 4° C.).

The extract was mixed with ammonium sulfate (35% of saturation), left for 1 h at 4° C., and further centrifuged, as above. The ammonium sulfate in the supernatants was then brought to 65% of saturation, left at 4° C. for 24 h and further centrifuged. Each pellet was dissolved in 1 M ammonium sulfate, 50 mM Tris-HCl, pH 8.0, and purified by hydrophobic interaction chromatography on Phenyl-Sepharose 6 Fast Flow (Pharmacia-Upjohn) (gradient elution, buffer A: 100 mM sodium phosphate, pH 8.0, containing 1 M ammonium sulfate; buffer B: 70% ethylen glycol, 5% methanol, 100 mM sodium phosphate, pH 8.0). Fractions containing hTNF immunoreactive material (by ELISA) were pooled, dialyzed against 20 mM Tris-HCl, pH 8.0 and further purified by ion exchange chromatography on DEAE-Sepharose Fast Flow (Pharmacia-Upjohn) (gradient elution, buffer A: 20 mM Tris-HCl, pH 8.0; buffer B: 1 M sodium chloride, 20 mM Tris-HCl, pH 8.0). All solutions employed in the chromatographic steps were prepared with sterile and endotoxin-free water (Salf, Bergamo, Italy).

At this point about 30 mg of TNF and 32 mg NGR-TNF was recovered from two-liters cultures. Non reducing SDS-PAGE showed bands corresponding to monomers, dimers and trimers suggesting that also human NGR-TNF was a mixture of trimers with correct intra-chain disulfides and trimers with one or more interchain disulfide bridges (FIG. 4A, lane b), as observed with murine NGR-TNF.

Trimers with correct intrachain disulfide bridges were isolated from this mixture by a four-step denaturation-refolding process as follows: purified human NGR-TNF was denatured with 7 M urea and gelfiltered through an HR Sephacryl S-300 column (1025 ml) (Pharmacia) pre-equilibrated with 7 M urea, 100 mM Tris-HCl, pH 8.0. Fractions corresponding to monomeric TNF were pooled, ultrafiltered through an YM MWCO 10 kDa membrane (Amicon) and refolded by dialysis against 33 volumes of 2.33 M urea, 100 mM Tris-HCl, pH 8 at 4° C. (140 min) followed by 1.55 M urea, 100 mM Tris-HCl, pH 8 (140 min) and 1 M urea, 100 mM Tris-HCl, pH 8 (140 min). Finally the product was dialyzed against 80 volumes of 100 mM Tris-HCl (16 h), centrifuged at 13000×g (30 min), filtered through a SFCA 0.45 μm membrane (Nalgene) and gelfiltered through an HR Sephacryl S-300 column (1020 ml) pre-equilibrated with 0.15 M sodium chloride, 0.05 M sodium phosphate (PBS). About 23 mg of refolded protein was recovered.

The final product was mostly monomeric after non reducing SDS-PAGE (FIG. 4A, lane c), had an hydrodynamic volume similar to that of trimeric human TNF by analytical gel-filtration HPLC on a Superdex 75 HR column (not shown), and had a molecular mass of 17937.8+1.8 Da (expected for CNGRCG-TNF1-157 (SEQ ID NO: 18), 17939.4 Da) by electrospray mass spectrometry. The in vitro cytolytic activities of non-refolded and refolded NGR-TNF on mouse L-M cells were $(6.11\times10^7)+4.9$ and $(5.09\times10^7)+0.3$ units/mg respectively, whereas that of purified human TNF was $(5.45\times10^7)+3.1$ units/mg. These results suggest that the denaturation-refolding process did not affect the interaction of human NGR-TNF with the murine p55 receptor.

Figure 4C:
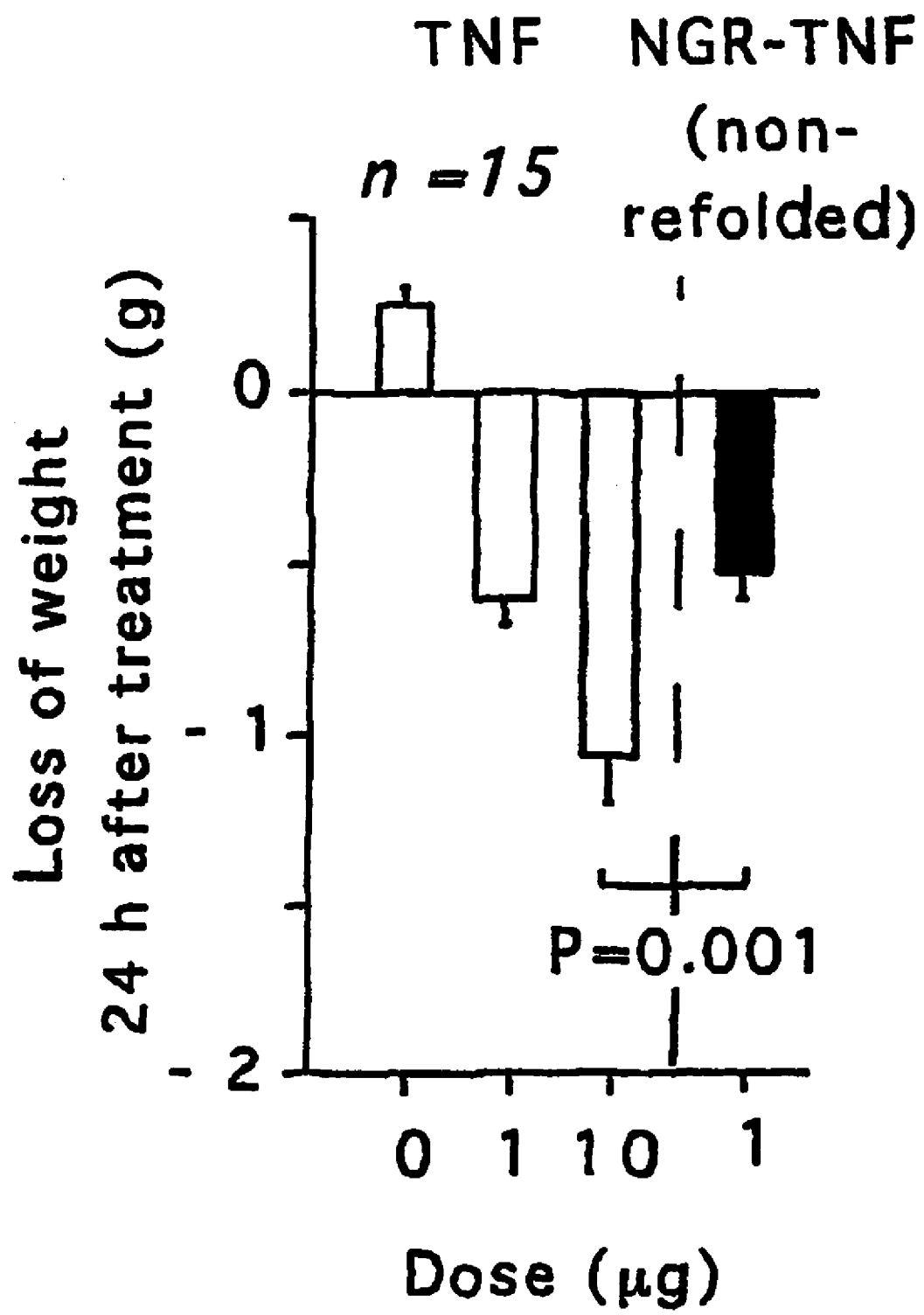
Figure 4E:
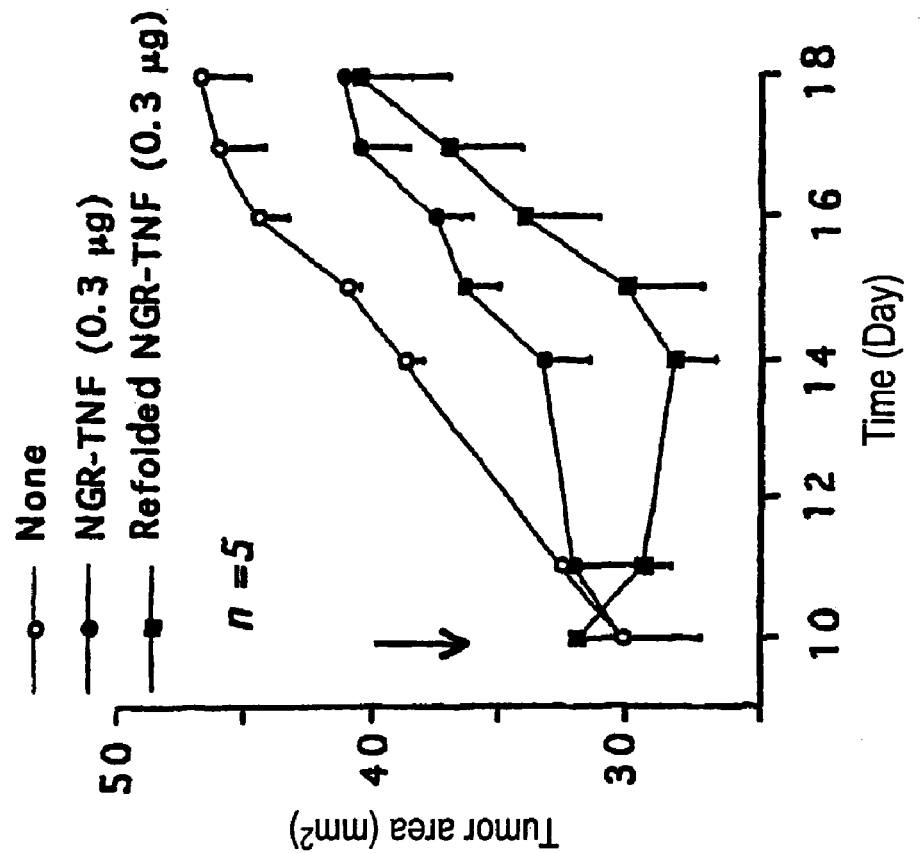
Figure 4D:
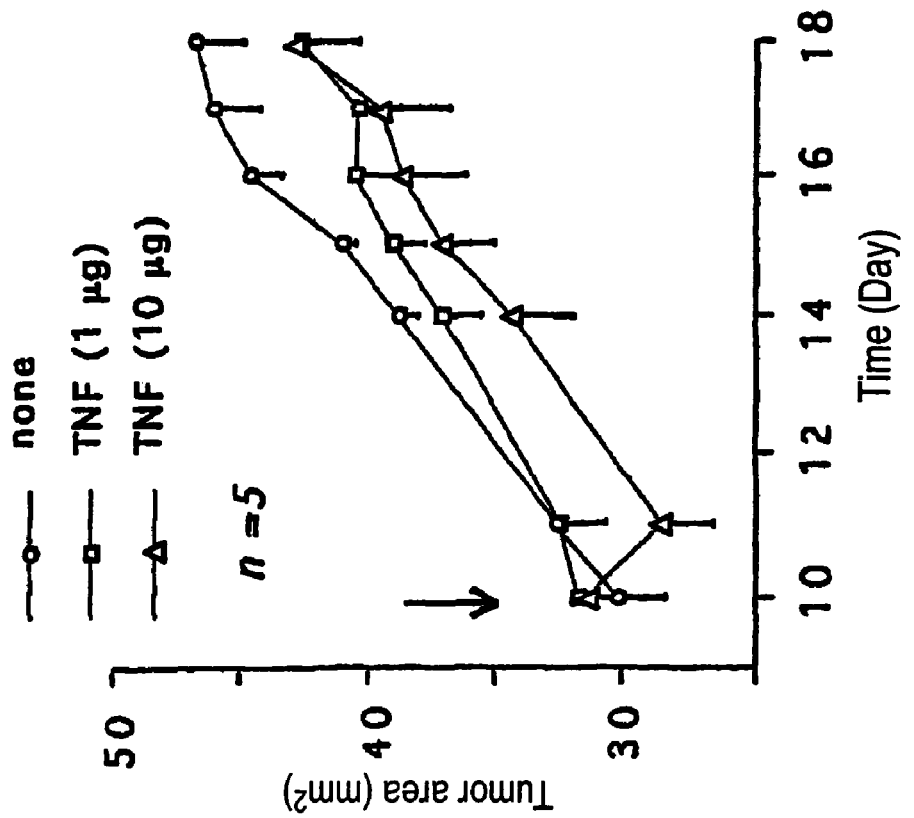

The in vivo anti-tumor activity of 1 µg of human NGR-TNF (non refolded) was greater than that of 10 µg of TNF (FIG. 4B) whereas the toxicity, as judged by animal weight loss, was significantly lower (FIG. 4C). After refolding 0.3 µg of NGR-TNF was sufficient to induce an anti-tumor effect stronger than that achieved with 10 µg of TNF (FIGS. 4D, 4E).

These results indicate that the anti-tumor activity of human NGR-TNF is greater than that of human TNF.

Furthermore, we have observed that refolded human and mouse NGR-TNF can induce significant anti-tumor effects on RMA-T-bearing mice even at very low doses (1-10 ng/mouse) with no evidence of toxic effects, while TNF was unable to induce significant effects at these doses (not shown).

EXAMPLE VI

Preparation and Characterization of Mouse NGR-IFNγ

Recombinant murine interferon (IFN)γ fused with CNGRCG (SEQ ID NO: 18) (NGR-IFNγ) was prepared by recombinant DNA technology, essentially as described for NGR-TNF. The CNGRC (SEQ ID NO: 5) domain was fused with the C terminus of IFNγ. Moreover the cysteine in position 134 was replaced with a serine; a methionine was introduced in position –1 for expression in *E.coli* cells. The PCR primers used for the production of the NGR-IFNγ cDNA were: 5'-A TAT CTA CAT ATG CAC GGC ACA GTC ATT GAA AGC C (sense) (SEQ ID NO: 12) and 5'-TC GGA TCC TCA GCA ACG GCC GTT GCA GCC GGA GCG ACT CCT TTT CCG CTT CCT GAG GC (SEQ ID NO: 13). The cDNA was cloned cloned in pET-11b (Nde I/BamH I) and used to transform BL21(DE3) *E.coli* cells (Novagen). Protein expression was induced with isopropyl-β-D-thiogalactoside, according to the pET11b manufacturer's instruction. The product was purified from *E.coli* extracts by immunoaffinity chromatography using an anti-mouse IFNγ mAb (AN18) immobilized on agarose, according to standard techniques. Reducing and non reducing SDS-PAGE of the final product showed a single band of 16 kDa. Electrospray mass spectrometry showed a molecular weight of 16223+3.6 Da (expected, 1625.5 Da) corresponding to murine Met-IFNγ1-134 (C134S)CNGRC (SEQ ID NO: 5) (NGR-IFNγ).

The capability of NGR-IFNγ and NGR-TNF to compete the binding of an anti-CD13 antibody to tumor associated vessels was investigated by using an immunohistochemical approach.

Fresh surgical specimens of human renal cell carcinoma were obtained from the Histopathology Department of the San Raffaele H Scientific Institute. Sections (5-6 µm thick) of Bouin-fixed (4-6 h) paraffin-embedded specimens were prepared and adsorbed on polylysine-coated slides. CD13 antigen were detected using the avidin-biotin complex method as follows: tissue sections were rehydrated using xylenes and graded alcohol series, according to standard procedures. Tissue sections were placed in a vessel containing 1 mM EDTA and boiled for 7 min using a micro-wave oven (1000 W). The vessel was then refilled with 1 mM EDTA and boiled again for 5 min. The tissue sections were left to cool and incubated in PBS containing 0.3% hydrogen peroxide for 15 min, to quench endogenous peroxidase. The samples were then and rinsed with PBS and incubated with 100-200 µl of PBS-BSA (1 h at room temperature) followed by the mAb WM15 (anti-hCD13), alone or mixed with various competitor agents (see Table 2) in PBS-BSA (overnight at 4° C.). The slides were then washed 3 times (3 min each) with PBS and incubated with PBS-BSA containing 2% normal horse serum (PBS-BSA-NHS) (Vector Laboratories, Burlingame, Calif.) for 5 min. The solution was then replaced with 3 µg/ml biotinylated horse anti-mouse IgG (H+L) (Vector Laboratories, Burlingame, Calif.) in PBS-BSA-NHS and further incubated for 1 h at room temperature. The slides were washed again and incubated for 30 min with Vectastain Elite Reagent (Vector Laboratories, Burlingame, Calif.) diluted 1:100 in PBS. A tablet of 3,3'-diamino-benzidine-tetrahydrocloride (Merck, Darmstadt, Germany) was then dissolved in 10 ml of deionized water containing 0.03% hydrogen peroxide, filtered through a 0.2 µm membrane and overlaid on tissue sections for 5-10 min. The slides were washed as above and counterstained with Harris' hematoxylin. The tumor associated vessels were identified by staining serial sections of the tissue with an anti-CD31 mAb (mAb JC/70A, anti-human CD31, IgG1, from DAKO, Copenhagen, Denmark).

The results are summarized in Table 2. As shown, the binding of WM15 to tumor associated vessels was inhibited by an excess of NGR-TNF, NGR-IFNγ and CNGRC (SEQ ID NO: 5), but not by other control reagents lacking the NGR motif. This suggests that the NGR binding site on CD13 sterically overlaps with the WM15 epitope. In contrast, NGR-TNF was unable to compete the binding of 13C03 to epithelial cells.

We conclude that the NGR moiety of NGR-IFNγ and NGR-TNF and can interact with a CD13 form recognized by mAb WM15 on tumor associated vessels. Moreover, these results indicate that the CNGRC (SEQ ID NO: 5) motif is functional either when linked to the N-terminus or the C-terminus of a cytokine.

TABLE 2

Binding of WM15 to renal cell cancer sections in the presence of various competitors

| Competitor | Binding of WM15 to tumor associated vessels |
|---|---|
| None | + |
| NGR-TNF (25 µg/ml) | − |
| NGR-IFNγ (50 µg/ml) | − |
| CNGRC (100 µg/ml) | − |
| TNF (25 µg/ml) | + |
| Human serum albumin (25 µg/ml) | + |
| Synthetic CgA(60-68) (100 µg/ml) | + |

[a] The competitor, in PBS containing 2% BSA, was added in the blocking step and mixed with the primary antibody.
[b] mAb WM15 (anti-human CD13, IgG1) was from Pharmingen (San Diego, CA); the synthetic peptide CgA(60-68) corresponds to the chromogranin A fragment 60-68.

EXAMPLE VII

Targeted Delivery of Biotinylated NGR-TNF to Tumors Using Anti-tumor Antibodies and Avidin (Pre-targeting)

The following example illustrates the possibility of "dual" targeting of TNF, based on the combination of a tumor homing antibody and the peptide CNGRC (SEQ ID NO: 5).

A biotin-NGR-TNF conjugate was prepared by mixing NGR-TNF with D-biotinyl-6-aminocaproic acid N-hydroxysuccinimide ester (Societa Prodotti Antibiotici S.p.A, Milan, Italy), in 1 M sodium-carbonate buffer, pH 6.8 (3 h at room temperature) (21). The reaction was blocked with 1 M Tris-HCl, pH 7.5.

The conjugate was characterized by mass spectrometry and found to contain 1 biotin/trimer (on average). C57BL/6 (Charles River Laboratories, Calco, Italy) were then challenged with $5 \times 10^4$ RMA-T living cells, s.c. in the left flank. When the tumor area reached 40 mm$^2$, mice were treated by sequential injections of biotinylated antibody, avidins and biotin-TNF according to a "three-day" protocol as described previously (26). We injected: 40 μg biotin-mAb19E12 (i.p., step I), 60 μg avidin and 60 μg streptavidin after 18 and 19 h, respectively (i.p., step II), 3 μg of biotin-NGR-TNF, 24 h later (i.p, step III). Each compound was diluted with a sterile 0.9% sodium chloride solution. In control experiment, avidin and streptavidin were omitted. Each experiment was carried out with 5 mice/group. The tumor growth was monitored daily by measuring the tumor size with calipers. The tumor areas before and 10 days after treatment were 39±4 mm$^2$ and 8±5 mm$^2$, respectively, in the group treated with mAb 19E 12-biotin/avidin/streptavidin/biotin-NGR-TNF (5 animals, mean±SE). In the control group (treated with mAb 19E12-biotin/biotin-NGR-TNF alone) the tumor areas before and 10 days after treatment were 40±4 mm$^2$ and 20±6 mm$^2$ respectively, indicating that pre-targeting with tumor homing antibody and avidin has increased the activity of NGR-TNF.

EXAMPLE VIII

Synergistic Activity Between NGR-TNF and Interferon-γ

Mouse B16F1 melanoma cells were cultured as described previously (Curnis et al., 2000; Moro et al., 1997).

The neutralizing anti-IFNgamma monoclonal antibody AN18 was kindly supplied by P.Dellabona, Milan, Italy). Doxorubicin (Adriblastina) was purchased from Pharmacia-Upjohn (Milan, Italy). Recombinant murine IFNγ was purchased from Peprotech Inc. (USA) (endotoxin content: <1 Units/μg). TS/A cells from a BALB/c spontaneous mammary adenocarcinoma were cultured in RPMI 1640 medium, 10% fetal bovine serum, 100 U/ml penicillin, 100 μg/ml streptomycin, 0.25 μg/ml amphotericin B, 2 mM glutamine and 1% minimal essential medium with nonessential amino acids (BioWhittaker Europe, Verviers, Belgium).

Murine TNF and NGR-TNF (consisting of TNF fused with the C-terminus of CNGRCG (SEQ ID NO: 18)) was prepared by recombinant DNA technology and purified from *E.coli* cell extracts, as described (Curnis, et al., 2000). All solutions used in the chromatographic steps were prepared with sterile and endotoxin-free water (Salf, Bergamo, Italy). Protein concentration was measured with a commercial protein quantification assay kit (Pierce, Rockford, Ill.). The cytolytic activity of NGR-mTNF was $9.1 \times 10^7$ Units/mg. The hydrodynamic volume of NGR-mTNF was similar to that of mTNF, a homotrimeric protein (Smith and Baglioni, 1987), by gel filtration chromatography on a Superdex 75 HR column (Pharmacia, Sweden). Endotoxin content of NGR-mTNF was 0.082 Units/pg.

DNA manipulations were performed by standard recombinant DNA methods. The cDNA coding for murine IFNγ was prepared by PCR on cDNA obtained from murine lymphocytes stimulated with phorbol 12-myristate 13-acetate, using the following primers: 5'A<u>GAATTC</u>ATGAACGCTACACACTGCATCTTGGC 3' (SEQ ID NO: 14) (forward primer); 5'TATATT<u>AAGCTT</u>TCAGCAGCGACTCCTTTTCCGC 3' (SEQ ID NO: 15) (reverse primer). Primers were designed to amplify the cDNA sequence coding for the full-length mouse IFNγ, including the leader sequence. They include the EcoRI and HindIII restriction site (underlined) for the cloning into the mammalian expression vector pRS1-neo, to generate pRS1neo-IFNγ. pRS1neo-IFNγ was then prepared using the Plasmid Maxi Kit (Qiagen Inc.-Diagen, GmbH, Germany) and diluted at 1 mg/ml in sterile and endotoxin-free water (S.A.L.F. Laboratorio Farmacologico SpA, Bergamo, Italy). pRS1neo-IFNγ (3 γg) was mixed with 100 μl of 0.03 mg/ml Lipofectin Reagent (Gibco Brl) in RPMI 1640 and incubated for 20 min at room temperature. Then the mixture was added to TS/A cells plated in 24-well microtiter plates 1 day before ($4 \times 10^4$ cells per well in 200 μl of culture medium). After incubation at 37° C., 5% CO$_2$ for 4 h, 2 ml of culture medium were added to each well. After 48 h of incubation the culture medium was changed with RPMI 1640 supplemented with 10% fetal bovine serum, 2 mM glutamine and containing 1 mg/ml geneticin. One week later, cells surviving selection were cloned by limiting dilution in 96-well microtiter plates in the presence of geneticin. The supernatants of each clone was tested by IFNγ-ELISA. Ten IFNγ-secreting clones were obtained. One clone, named TS/A-IFNγ, producing 1.13 μg IFNγ per ml of culture medium was selected and used for in vivo experiments.

IFNγ-ELISA. PVC microtiter plates (Becton Dickinson, cod.3912) were coated with 5 μg/ml mAb AN18 in PBS (16 h at 4° C.). Plates were washed three times with PBS and blocked with 2% bovine serum albumin (BSA) in PBS (PBS-BSA, 1 h at 37° C.). Plates were then washed three times with PBS and incubated with cell culture supernatants or mouse IFNγ standard solutions diluted in PBS-BSA. Plates were washed eight times with PBS containing 0.05% Tween-20 (Merck) (PBS-TW) and incubated with mAb XMG1.2-bio (0.2 μg/ml in PBS, 1 h at 37° C.). Plates were washed again with PBS-TW and incubated for 1 h at 37° C. with streptavidin-horseradish peroxidase (Sigma) diluted 1:3000 in PBS-BSA. After washing with PBS-TW, bound peroxidase was detected with o-phenylenediamine dihydrochloride peroxidase substrate (Sigma). The chromogenic reaction was blocked after 30 min by adding 10% sulfuric acid. The $A_{490}$ was measured with an ELISA microplate reader (Biorad).

Studies on animal models were approved by the Ethical Committee of the San Raffaele H Scientific Institute and performed according to the prescribed guidelines. C57BL/6 mice (Charles River Laboratories, Calco, Italy) weighing 16-18 g were challenged with subcutaneous injection in the left flank of $5 \times 10^4$ or B16F1 living cells; 5 days later, the mice were treated with NGR-mTNF and mIFNγ solutions (100 μl) followed 2 h later by administration of doxorubicin solution (100 μl). All drugs were administered intraperitoneally (i.p). The drugs were diluted with 0.9% sodium chloride, containing 100 μg/ml endotoxin-free human serum albumin (Farma-Biagini, Lucca, Italy), except for doxorubicin, which was diluted with 0.9% sodium chloride alone. Tumor growth was monitored daily by measuring the tumors with calipers as previously described (Gasparri et al., 1999). Animals were sacrificed before the tumors reached 1.0-1.5 cm in diameter. Tumor sizes are shown as mean±SE (5 animals/group).

Endogenous IFN is Critical for NGR-TNF/Doxorubicin Therapeutic Activity.

We have shown previously that NGR-mTNF and doxorubicin play synergistic effects in B16-F1 tumor-bearing immunocompetent mice, the anti-tumor activity of doxorubinin being significantly increased by pre-administration of 0.1 ng of NGR-mTNF (above and Curnis et al., 2002). Accordingly, administration of low amounts of NGR-mTNF (0.1 ng) in combination with doxorubicin (80 µg) to B16-F10 tumor-bearing mice induced anti-tumor effects stronger than those obtained with doxorubicin alone (FIG. 5). These drugs act synergistically, as NGR-TNF alone is poorly active when used at low dosage (0.1 ng) (Curnis et al., 2002).

To assess the functional importance of endogenous mIFNγ in the anti-tumor activity of NGR-mTNF in immunocompetent mice, we studied the effect of a neutralizing anti-mIFNγ antibody (mAb AN18) on the anti-tumor activity of NGR-mTNF/doxorubicin in C57BL6 mice.

When this antibody was administered 24 h before NGR-mTNF, the synergistic effect between NGR-mTNF and doxorubicin was abolished (FIG. 5), supporting the hypothesis that endogenous mIFNγ is an important player in the anti-tumor activity of NGR-mTNF.

To further support the role of IFN in the therapeutic response to these drugs we performed other in vivo experiments using BALB/c IFNγ$^{-/-}$ "knock out" mice, bearing subcutaneous mouse TS/A-mammary adenocarcinoma tumors. In parallel, we performed similar experiments using wild-type BALB/c IFNγ$^{+/+}$ mice. NGR-TNF/doxorubicin significantly reduced the tumor mass in BALB/c IFNγ$^{+/+}$ mice (FIG. 6, black bars), but not in BALB/c IFNγ$^{-/-}$ mice (white bars). Notably, administration of exogenous IFN (300 ng) in combination with NGR-TNF and doxorubicin to BALB/c IFNγ$^{-/-}$ mice restored the synergy between these drugs (FIG. 6, white bars). These results confirm the hypothesis that IFN is necessary for the NGR-TNF/doxorubicin synergistic activity. Co-administration of IFN and doxorubicin without NGR-TNF did not induce significant anti-tumor effects in BALB/c IFNγ$^{-/-}$ mice (FIG. 6, white bars) indicating that this cytokine acts synergistically with NGR-TNF, and little or not with doxorubicin.

Role of T-cells and Locally Produced IFN in NGR-TNF/Doxorubicin Therapeutic Activity.

T- and NK-cells are the primary sources of IFN in immunocompetent mice. To investigate the importance of T-cells as a source of the IFN in the NGR-TNF/doxorubicin combined therapy we investigated the effect of these drugs in B16F1 tumor-bearing nu/nu mice, lacking T-cells. In this model the NGR-TNF/doxorubicin synergistic activity was lost (FIG. 7A-C). However, when these drugs were administered in combination with IFN, the synergistic effect was observed again (FIG. 7D). It is likely that the amount of endogenous IFN in these animals was not sufficient to activate the NGR-TNF/doxorubicin synergism, while administration of exogenous IFN restored the synergy.

The results of in vivo experiments with immunocompetent and nu/nu mice may suggest that T-cells present within the tumor mass of immunocompetent mice, but not of nu/nu mice, produce sufficient amounts of IFN to stimulate a synergistic response between NGR-TNF and chemotherapy. To assess whether the production of IFN within the tumor microenvironment could restore the synergistic effect in nu/nu mice, we transfected TS/A cells with murine IFN cDNA (FIG. 8). One clone able to secrete IFN in culture medium was selected and named TS/A-IFN. TS/A-IFN and wild-type TS/A cells were then implanted, subcutaneously, in nu/nu mice. As expected, NGR-TNF/doxorubicin exerted significant anti-tumor effects against TSA-IFN, but not against TS/A tumors, strongly suggesting that locally produced IFN is indeed critical for the NGR-TNF/doxorubicin synergism.

In conclusion, these and the above results indicate that the therapeutic activity of NGR-TNF/doxorubicin strongly depends on local production of IFN, likely secreted by tumor-infiltrating lymphocytes.

Exogenous IFN Enhances the Therapeutic Activity of NGR-TNF/Doxorubicin in Immunocompetent Mice.

The therapeutic activity of NGR-TNF and doxorubicin, in combination with exogenous IFN, (300 ng) was then evaluated using C57B16 mice bearing B16F1 tumors. As shown in FIG. 9, the anti-tumor activity of the triple combination was greater than that of NGR-TNF/doxorubicin. Thus, administration of exogenous IFN, together with NGR-TNF/doxorubicin, induced stronger anti-tumor effect also in immunocompetent mice.

Mechanism of Action of the Triple Combination (IFN, NGR-TNF and Doxorubicin).

We have shown previously that an important mechanism for the NGR-TNF/doxorubicin synergism is related to alteration of endothelial barrier function by NGR-TNF and increased penetration of doxorubicin in tumors. Thus, we investigated whether IFN is critical for this effect. To this aim we measured the effect of exogenous IFN on the penetration of doxorubicin in TS/A tumors (FIG. 10). This experiment takes advantage from the fact doxorubicin is a fluorescent compound and that the fluorescence intensity of tumor cells, recovered from animals after treatment, is an indication of the amount of doxorubicin that has penetrated tumors. The experiment was carried out in nu/nu mice to reduce the effect of endogenous IFN. When tumor-bearing mice were treated with NGR-TNF and, 2 h later, with doxorubicin, no significant increase of doxorubicin was found in tumor cells, compared to untreated controls. However, administration of IFN in combination with NGR-TNF increased the penetration of doxorubicin in tumors. This suggests that IFN is critical for the TNF-induced penetration of chemotherapeutic drugs.

The results of this study suggest that endogenous IFN is critical for the NGR-TNF/doxorubicin synergistic activity and that exogenous mIFNγ together with NGR-mTNF induce stronger anto-timour effect in both immunodeficient and immunocompetent mice. This view is supported by the above observations that a) a neutralizing anti-IFN antibody markedly inhibits the NGR-TNF/doxorubicin synergistic activity in immunocompetent mice and b) no synergism occurs in mice lacking the IFN gene (IFN−/− mice).

Given that T- and NK-cells are the primary sources of IFN in immunocompetent mice and that athymic nu/nu mice lack T-cells, the above results strongly suggest that T cells are the main source of the IFN necessary for NGR-TNF/doxorubicin activity. In accord with this view is the finding that exogenous or endogenous IFN (produced by tumor cells transfected with IFN cDNA) restore the NGR-TNF/doxorubicin synergistic activity in nu/nu mice.

These results point to a crucial role for IFN in tumor vascular targeting with NGR-TNF and doxorubicin.

The lack of therapeutic effects of IFN in combination with doxorubicin (without NGR-TNF) suggest this cytokine synergizes with NGR-TNF, and little or not with doxorubicin.

Considering that chemotherapeutic drugs must cross the vessel wall and migrate through the interstitium to reach the cancer cells, the site of action of IFN and NGR-TNF is very likely the endothelial lining of vessels. It is well known that TNF can induce, in endothelial cells, alteration of cytoskeletal actin and formation of intercellular gaps leading to increased permeability to macromolecules. On the same cells TNF can induce leukocyte adhesion molecules, proinflammatory cytokines, fibrin deposition, nitric oxide production, and apoptosis. Accordingly, we found that the in vitro permeability of eA endothelial cell monolayers to horseradish peroxidase was enhanced by exposure to TNF in combination with IFN compared to TNF alone. We cannot exclude that, in view of the various effects that both TNF and IFN can exert on endothelial cells, alteration of vascular permeability in vivo could be also the consequence of indirect effects related to local release of other important inflammatory molecules that affect endothelial permeability.

Our findings may also have other important implications. Several studies in animal models and in patients showed that TNF can selectively affect and damage tumor vessels but not vessels associated to normal tissues. Accordingly, the micro- and macrovasculature of tumors, but not of normal tissue, has been observed to be extensively damaged after patients were given isolated limb perfusion with TNF in combination with and melphalan. The molecular basis of this selectivity is unclear. It has been hypothesized that structural differences within tumor vessels and/or the presence of tumor derived-"sensitizing factors" could be responsible for the TNF vascular selectivity. Our results suggest local production of IFN, could be one of these sensitizing factors.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

REFERENCES

1. Carswell, E. A., et al., An endotoxin-induced serum factor that causes necrosis of tumors. Proc. Natl. Acad. Sci. USA 1975. 72:3666-70.
2. Helson, L., et al., Effect of tumor necrosis factor on cultured human melanoma cells. Nature 1975. 258:731-732.
3. Tracey, K. J., and A. Cerami. Tumor necrosis factor, other cytokines and disease. Ann. Rev. Cell Biol, 1993. 9:317-43.
4. Hoogenboom, H. R., et al., Construction and expression of antibody-tumor necrosis factor fusion proteins. Mol. Immunol. 1991. 28:1027-37.
5. Loetscher, H., et al., Human tumor necrosis factor alpha (TNF alpha) mutants with exclusive specificity for the 55-kDa or 75 kDa TNF receptors. J. Biol. Chem. 1993. 268:26350-7.
6. Yang, J., et al., A genetically engineered single-chain FV/TNF molecule possesses the anti-tumor immunoreactivity of FV as well as the cytotoxic activity of tumor necrosis factor. Mol. Immunol. 1995. 32:873-81.
7. Van Ostade, X., et al., Human TNF mutants with selective activity on the p55 receptor. Nature 1993. 361:266-9.
8. Paganelli, G., et al., Three-step monoclonal antibody tumor targeting in carcinoembryonic antigenpositive patients. Cancer Res. 1991. 51:5960-6.
9. Paganelli, G., et al., Clinical application of the avidin-biotin system for tumor targeting. In D. Goldenberg (Ed. Cancer therapy with radiolabeled antibodies. CRC Press, Boca Raton, 1995. P. 239-253.
10. Modorati, G., et al., Immunoscintigraphy with three step monoclonal pretargeting technique in diagnosis of uveal melanoma: preliminary results. Br. J. Ophtalm. 1994. 78:19-23.
11. Colombo, P., et al., Immunoscintigraphy with anti-chromogranin A antibodies in patients with endocrine/neuroendocrine tumors. J. Endocr. Invest. 1993. 16:841-3.
12. Debs, R. J., et al., Liposome-associated tumor necrosis factor retains bioactivity in the presence of neutralizing anti-tumor necrosis factor antibodies. J. Immunol. 1989. 143:1192-7.
13. Debs, R. J., et al., Immunomodulatory and toxic effects of free and liposome-encapsulated tumor necrosis factor alpha in rats. Cancer Res. 1990. 50:375-80.
14. Moro, M., et al., Tumor cell targeting with antibody-avidin complexes and biotinylated tumor necrosis factor alpha. Cancer Res. 1997. 57:1922-8.
15. Schraffordt Koops, et al., Hyperthermic isolated limb perfusion with tumour necrosis factor and melphalan as treatment of locally advanced or recurrent soft tissue sarcomas of the extremities. Radiothepray & Oncology 1998. 48:1-4.
16. Lienard, D., et al., In transit metastases of malignant melanoma treated by high dose rTNF alpha in combination with interferon-gamma and melphalan in isolation perfusion. World Journal of Surgery 1992. 16:234-40.
17. Hill, S., et al., Low-dose tumour necrosis factor alpha and melphalan in hyperthermic isolated limb perfusion. Br. J. Sugr. 1993. 80:995-7.
18. Eggermont, A. M., et al., Isolated limb perfusion with tumor necrosis factor and melphalan for limb salvage in 186 patients with locally advanced soft tissue extremity sarcomas. The cumulative multicenter European experience. Ann. Surg. 1996. 224:756-65.
19. Mizuguchi, H., et al., Tumor necrosis factor alpha-mediated tumor regression by the in vivo transfer of genes into the artery that leads to tumor. Cancer Res. 1998. 58:5725-30.
20. Pennica, D., et al., Cloning and expression in *Escherichia coli* of the cDNA for murine tumor necrosis factor. Proc. Natl Acad. Sci. USA 1985. 82:6060-4.
21. Corti, A., et al., Tumor targeting with biotinylated tumor necrosis factor alpha: Structure activity relationships and mechanism of action on avidin pretargeted tumor cells. Cancer Res. 1998. 58:3866-3872.
22. Corti, A., et al., Up-regulation of p75 Tumor Necrosis Factor alpha receptor in Mycobacterium avium-infected mice. Infect. Immun. 1999, 67:5762-5767.
23. Corti, A., et al., Tumor necrosis factor (TNF) alpha quantification by ELISA and bioassay: effects of TNF alpha-soluble TNF receptor (p55) complex dissociation during assay incubations. J. Immunol. Meth. 1994. 177:191-198.
24. Ljunggren, H. G., and K. Karre. Host resistance directed selectively against H-2-deficient lymphoma variants. Analysis of the mechanism. J. Exp. Med. 1985. 162:1745-59.
25. Celik, C., et al., Demonstration of immunogenicitywith the poorly immunogenic B16 melanoma. Cancer Res. 1983. 43:3507-10.

26. Gasparri, A., et al., Tumor pretargeting with avidin improves the therapeutic index of biotinylated tumor necrosis factor alpha in mouse models. Cancer Res. 1999. 59:2917-23.
27. Palladino, M. A., Jr., et al., Characterization of the antitumor activities of human tumor necrosis factor-alpha and the comparison with other cytokines: induction of tumor-specific immunity. J. Immunol. 1987. 138:4023-32.
28. Arap, W., et al., Cancer treatment by targeted drug delivery to tumor vasculature in a mouse model. Science 1998. 279:377-80.
29. Fiers, W. Biologic therapy with TNF: preclinical studies. In V. DeVita, S. Hellman, and S. Rosenberg Eds). Biologic therapy of cancer: principles and practice. J. B. Lippincott Company, Philadelphia, 1995. P. 295-327.
30. Rathjen, D. A., et al., 1992. Selective enhancement of the tumour necrotic activity of TNF alpha with monoclonal antibody. Brit. J. Cancer 65:852.
31. Robert, B., et al., 1996. Cytokine targeting in tumors using a bispecific antibody directed against carcinoembryonic antigen and tumor necrosis factor alpha. Cancer Res. 56:4758.
32. Fraker, D. L., Alexander, H. R. & Pass, H. I., 1995. Biologic therapy with TNF: systemic administration and isolation-perfusion. In *Biologic therapy of cancer: principles and practice*, DeVita, V., Hellman, S. & Rosenberg, S. (eds) pp. 329-345. J. B. Lippincott Company: Philadelphia.
33. Pennica, D., et al., 1984. Human tumor necrosis factor: precursor, structure, expression and homology to lymphotoxin. *Nature*, 321, 724-729.
34. Curnis, F., Sacchi, A., Borgna, L., Magni, F., Gasparri, A., and Corti, A. (2000). *Nat. Biotechnol.* 18, 1185-90.
35. Curnis, F., Sacchi, A., and Corti, A. (2002). *Journal of Clinical Investigation*, In press.
36. Gasparri, A., Moro, M., Curnis, F., Sacchi, A., Pagano, S., Veglia, F., Casorati, G., Siccardi, 36. A. G., Dellabona, P., and Corti, A. (1999). *Cancer Research* 59,2917-23.
37. Moro, M., Pelagi, M., Fulci, G., Paganelli, G., Dellabona, P., Casorati, G., Siccardi, A. G., and Corti, A. (1997). *Cancer Research* 57, 1922-8.
38. Smith, R. A., and Baglioni, C. (1987). *Journal of Biological Chemistry* 262, 6951-4.

The invention claimed is:

1. A method of treating or diagnosing a cancer patient comprising administering simultaneously, sequentially or separately: (a) an effective amount of a conjugation product of TNF and a ligand of the CD13 receptor, wherein the ligand is a peptide comprising the NGR motif, and (b) an effective amount of IFNγ.

2. The method as claimed in claim 1, wherein said TNF is TNFα or TNFβ.

3. The method as claimed in claim 1, wherein said peptide comprises a sequence selected from the group consisting of CNGRCVSGCAGRC (SEQ ID NO:1), NGRAHA (SEQ ID NO:2), GNGRG (SEQ ID NO:3), CNGRCG (SEQ ID NO:18), cycloCVLNGRMEC (SEQ ID NO:4), linear CNGRC (SEQ ID NO:5), and cyclic CNGRC (SEQ ID NO:6).

4. The method as claimed in claim 3, wherein the TNF is linked to the peptide through a spacer.

5. The method as claimed in claim 3, wherein the conjugation product is between TNF and linear or cyclic CNGRC and wherein the amino-terminal of TNF is linked to the peptide through the spacer G.

6. The method as claimed in claim 1, wherein the TNF is derivatized with polyethylene glycol or an acyl residue.

7. The method as claimed in claim 1, wherein the TNF is further conjugated with an antibody or fragment thereof, wherein said antibody or fragment thereof is directed to a compound selected from the group consisting of a tumoral antigen, a tumoral angiogenic marker, and a component of the extracellular matrix.

8. The method according to claim 7, wherein the TNF is conjugated to both a peptide comprising the NGR motif and an antibody or fragment thereof on different subunits.

9. The method as claimed in claim 1, wherein the conjugation product of TNF and the peptide comprising the NGR motif and the IFNγ are in the form of an injectable solution or suspension or a liquid for infusion.

10. The method as claimed in claim 1, wherein the conjugation product of TNF and the peptide comprising the NGR motif and the IFNγ are in the form of liposomes.

11. The method of claim 1 comprising additionally administering other antitumor agents or diagnostic tumor-imaging compounds.

* * * * *